US010881647B2

(12) United States Patent
Berde et al.

(10) Patent No.: US 10,881,647 B2
(45) **Date of Patent: *Jan. 5, 2021**

(54) NEOSAXITOXIN COMBINATION FORMULATIONS FOR PROLONGED LOCAL ANESTHESIA

(71) Applicant: The Children's Medical Center Corporation, Boston, MA (US)

(72) Inventors: Charles Berde, Bookline, MA (US); Daniel S. Kohane, Newton, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/396,071

(22) Filed: Apr. 26, 2019

(65) Prior Publication Data

US 2019/0247377 A1 Aug. 15, 2019

Related U.S. Application Data

(63) Continuation of application No. 14/216,252, filed on Mar. 17, 2014, now Pat. No. 10,314,833.

(60) Provisional application No. 61/789,054, filed on Mar. 15, 2013.

(51) Int. Cl.

| | |
|---|---|
| ***A61K 31/445*** | (2006.01) |
| ***A61K 31/52*** | (2006.01) |
| ***A61P 43/00*** | (2006.01) |
| ***A61K 31/519*** | (2006.01) |
| ***A61K 31/245*** | (2006.01) |
| ***A61K 31/137*** | (2006.01) |
| ***A61K 9/00*** | (2006.01) |

(52) U.S. Cl.

CPC .......... *A61K 31/445* (2013.01); *A61K 9/0019* (2013.01); *A61K 31/137* (2013.01); *A61K 31/245* (2013.01); *A61K 31/519* (2013.01); *A61K 31/52* (2013.01); *A61P 43/00* (2018.01)

(58) Field of Classification Search

None

See application file for complete search history.

(56) References Cited

U.S. PATENT DOCUMENTS

| | | | |
|---|---|---|---|
| 3,004,894 | A | 10/1961 | Johnson |
| 3,328,259 | A | 6/1967 | Anderson |
| 3,374,144 | A | 3/1968 | Emmanuel |
| 3,957,996 | A | 5/1976 | Adams |
| 3,966,934 | A | 6/1976 | Adams |
| 4,001,413 | A | 1/1977 | Adams |
| 4,022,899 | A | 5/1977 | Adams |
| 4,029,793 | A | 6/1977 | Adams |
| 4,029,794 | A | 6/1977 | Adams |
| 4,313,958 | A | 2/1982 | LaHann |
| 4,401,663 | A | 8/1983 | Buckwalter |
| 4,443,473 | A | 4/1984 | Buckwalter |
| 4,460,602 | A | 7/1984 | Buckwalter |
| 4,493,848 | A | 1/1985 | LaHann |
| 4,537,776 | A | 8/1985 | Cooper |
| 4,544,668 | A | 10/1985 | Janusz |
| 4,544,669 | A | 10/1985 | LaHann |
| 4,564,633 | A | 1/1986 | LaHann |
| 4,654,323 | A | 3/1987 | Beitner |
| 4,820,720 | A | 4/1989 | Sanders |
| 4,863,970 | A | 9/1989 | Patel |
| 4,973,468 | A | 11/1990 | Chiang |
| 4,997,853 | A | 3/1991 | Bernstein |
| 5,006,342 | A | 4/1991 | Cleary |
| 5,008,289 | A | 4/1991 | Bernstein |
| 5,013,759 | A | 5/1991 | Berman |
| 5,045,565 | A | 9/1991 | Gardner |
| 5,099,030 | A | 3/1992 | Gardner |
| 5,134,166 | A | 7/1992 | Bernstein |

(Continued)

FOREIGN PATENT DOCUMENTS

| | | |
|---|---|---|
| BE | 776769 | 12/1971 |
| EP | 0043738 | 9/1982 |

(Continued)

OTHER PUBLICATIONS

Aboul-Fadl, "Antisense oligonucleotides: the state of the art", Curr Med Chem 12:2193-214 (2005).

(Continued)

*Primary Examiner* — Kortney L. Klinkel
*Assistant Examiner* — William Y Lee
(74) *Attorney, Agent, or Firm* — Pabst Patent Group LLP

(57) ABSTRACT

Since each of the site I sodium channel blockers have a unique activity and cannot be used to extrapolate the same effective dosage for another site I sodium channel blocker, studies were conducted to identify dosages of neosaxitoxin ("NeoSTX") and bupivacaine, alone or in combination with epinephrine, to provide two to three days of pain relief in humans. Bupivacaine-NeoSTX combinations produce more reliable blockade and longer duration blockade compared to NeoSTX alone. The three-way combination of NeoSTX-bupivacaine-epinephrine produces more prolonged local anesthesia than the two-way combination of NeoSTX-bupivacaine. Addition of epinephrine to this NeoSTX-bupivacaine combination dramatically prolongs the duration of complete blockade to a mechanical stimulus. These results led to development of specific combination dosage formulations.

14 Claims, 11 Drawing Sheets

(56) References Cited

U.S. PATENT DOCUMENTS

| | | | | |
|---|---|---|---|---|
| 5,618,563 | A | 4/1997 | Berde | |
| 5,700,485 | A | 12/1997 | Berde | |
| 5,716,637 | A | 2/1998 | Anselem | |
| 5,858,397 | A | 1/1999 | Lim | |
| 6,030,974 | A | 2/2000 | Schwartz | |
| 6,326,020 | B1 | 12/2001 | Kohane | |
| 6,407,088 | B1 | 6/2002 | Dong | |
| 6,455,066 | B1 | 9/2002 | Fischer | |
| 6,673,363 | B2 | 1/2004 | Luo | |
| 8,975,268 | B2 | 3/2015 | Berde | |
| 8,975,281 | B2 | 3/2015 | Berde | |
| 10,314,833 | B2 * | 6/2019 | Berde | A61K 31/445 |
| 2002/0161013 | A1 | 10/2002 | Liu | |
| 2002/0197284 | A1 | 12/2002 | Luo | |
| 2003/0152637 | A1 | 8/2003 | Chasin | |
| 2004/0172354 | A1 | 9/2004 | Charnley | |
| 2005/0202093 | A1 | 9/2005 | Kohane | |
| 2005/0214325 | A1 | 9/2005 | David | |
| 2006/0271466 | A1 | 11/2006 | Gorbatovsky | |
| 2008/0045553 | A1 | 2/2008 | Wilson | |
| 2008/0154792 | A1 | 6/2008 | Maggioncalda | |

FOREIGN PATENT DOCUMENTS

| | | |
|---|---|---|
| EP | 750909 | 1/1997 |
| GB | 1370904 | 10/1974 |
| GB | 2153223 | 8/1985 |
| WO | 8505621 | 12/1985 |
| WO | 9311798 | 6/1993 |
| WO | 9401166 | 1/1994 |
| WO | 9405265 | 3/1994 |
| WO | 9641616 | 12/1996 |
| WO | 9851290 | 11/1998 |
| WO | 0141550 | 6/2001 |
| WO | 0222129 | 3/2002 |
| WO | 0241915 | 5/2002 |
| WO | 2003047589 | 6/2003 |
| WO | 2006034624 | 4/2006 |
| WO | 2006091719 | 8/2006 |
| WO | 2008063603 | 5/2008 |
| WO | 2009143174 | 11/2009 |
| WO | 2009143175 | 11/2009 |
| WO | 2010041255 | 4/2010 |
| WO | 2010109386 | 9/2010 |
| WO | 2010109387 | 9/2010 |
| WO | 2010117996 | 10/2010 |
| WO | 2010129864 | 11/2010 |
| WO | 2011098539 | 8/2011 |

OTHER PUBLICATIONS

Akerman, et al., "Penetration enhancers and othe factors governing percutaneous local anaesthesia with lidocaine", Acta Pharma. Et toxicological, 45(1):58-65 (1979).

Adjei and Garren, "Pulmonary delivery of peptide drugs: effect of particle size on bioavailability of leuprolide acetate in healthy male volunteers" , J Pharm. Res, 7:565-9 (1990).

Alam, et al., "Design of liposome to improve encapsulation efficiency of gelonin and its effect on immunoreactivity and ribosome inactivating property" , Mol Cell Biochem 112:97-107 (1992).

Barnes, "Sativex: clinical efficacy and tolerability in the treatment of symptoms of multiple sclerosis and neuropathic pain" , Expert Opin Pharmacother 7:607-15 (2006).

Barnet, et al., "Tissue injury from tricyclic antidepressants used as local anesthetics" Anesth Analg, 101(6):1838-1843 (2005).

Barnet, et al., "Site 1 sodium channel blockers prolong the duration of sciatic nerve blockade from tricyclic antidepressants", Pain 110:432-8 (2004).

Bartlett, "Phosphorus assay in column chromatography", J. Biol. Chem., 234(3):466-468 (1959).

Bates, et al., "A chemical assay for saxitoxin. Improvements and modifications", J. of agricultural and food chem., 26(1):252-254 (1978).

Befort, et al., "Selective up-regulation of the growth arrest DNA damage-inducible gene Gadd45 alpha in sensory and motor neurons after peripheral nerve injury", Eur J Neurosci., 18(4):911-922 (2003).

Benoit, et al., "Pharmacologic correlation between local anesthetic-induced myotoxicity and disturbances of intracellular calcium distribution", Toxicol. Appl. Pharmacol., 52:187-198 (1980).

Berde, et al., "Tetrodotoxin-bupivacaine-epinephrine combinations for prolonged local anesthesia", Marine Drugs, 9:2717-28 (2011).

Bernards and Hill, "Physical and chemical properties of drug molecules governing their diffusion through the spinal meninges", Anesthesiology, 77(4):750-6 (1992).

Binshtok, et al., "Inhibition of nociceptors by TRPV1-mediated entry of impermeant sodium channel blockers", Nature, 449:607-610 (2007).

Bolch and Blackburn, "Isolation and purification of Australian isolates of the toxic cyanobacteriumMicrocystis aeruginosa Kütz", J. Appl. Phycology, 8, 5-13 (1996).

Castro, et al., "the effect of temperature on growth and production of paralytic shellfish poisoning toxins by the cyanobacterium Cylindrospermopsis raciborskii C10", Toxicon, 44:483-89 (2004).

Cereda, et al., "Liposomal formulations of prilocaine, lidocaine and mepivacaine prolong analgesic duration", Can J Anaesth., 53(11):1092-1097 (2006).

Chaim-Matyas, et al., "Encapsulation of the cobra cytotoxin P4 in liposomes", Biotechnol Appl Biochem, 17( Pt 1):31-6 (1993).

Choi and Maibach, "Liposomes arid niosomes as topical drug delivery systems", J, Pharmacal and Biophys. Res.,18(5):209-19 (2005).

Clarkson, et al., "Mechanism for bupivacaine depression of cardiac conduction: fast block of sodium channels during the action potential with slow recovery from block during diastole", Anesthesiology, 62:396-405 (1985).

Cortesi, et al., "Sugar cross-linked gelatin for controlled release: microspheres and disks", Biomaterials 19:1641-9 (1998).

De Araujo, et al., "Encapsulation of mepivacaine prolongs the analgesia provided by sciatic nerve blockade in mice", Can J Anaesth., 51(6):566-572 (2004).

De Paiva and Dolly, "Light chain of botulinum neurotoxin is active in mammalian motor nerve terminals when delivered via liposomes", FEBS Lett 277:171-4 (1990).

Drager, et al., Prolonged intercostal nerve blockade in sheep using controlled-release of bupivacaine and dexamethasone from polymer microspheres Anesthesiology, 89(4):969-979 (1998).

Epstein-Barash, et al., "Prolonged duration local anesthesia with minimal toxicity", PNAS, 106(17):7125-30 (2009).

Estebe, et al., "Amitriptyline neurotoxicity: dose-related pathology after topical application to rat sciatic nerve", Anesthesiology, 100:1519-25 (2004).

Fang, et al., "Synergistically enhanced transdermal prrmration and tropical analgesia of tetracaine gel containing menthol and ethanol in experimental and clinical studies", Eu J Pharm and Biopharm., 68:735-40 (2008).

Fisher, et al., "Detection of intravascular injection of regional anaesthetics in children", Can. J. Anaesth., 44: 592-8 (1997).

Flores, Production of ammonium dependent on basic L-amino acids vy anacystis nidulans, Arch Microbiol, 131:91-4 (1982).

Fozzard, et al., "Mechanism of local anesthetic drug action on voltage-gated sodium channels", Curr. Pharm. Des., 11:2671-2686 (2005).

Fraser, et al., "Intravesical liposome administration—a novel treatment for hyperactive bladder in the rat", Urology, 61: 656-663 (2003).

Freitas and Frezard, "Encapsulation of native crotoxin in liposomes: a safe approach for the production of antivenom and vaccination against Crotalus durissus terrificus venom", Toxicon 35:91-100 (1997).

Garcia, et al., "Route of metabolization and detoxicarion of paralytric shellfish toxins in humans", Toxicon, 55:135-44 (2010).

Gerner, et al., "Amitriptyline versus bupivacaine in rat sciatic nerve blockade", Anesthesiology, 94(4):661-667 (2001).

(56) References Cited

OTHER PUBLICATIONS

Grant, et al., "A novel liposomal bupivacaine formulation to produce ultralong-acting analgesia", Anesthesiology, 101(1):133-137 (2004).
Grant, et al., "Analgesic duration and kinetics of liposomal bupivacaine after subcutaneous injection in mice", Clin Exp Pharmacol Physiol., 30(12):966-968 (2003).
Grant, et al., "DRV liposomal bupivacaine: preparation, characterization, and in vivo evaluation in mice", Pharm Res., 18(3):336-343 (2001).
Gregoradis, et al., "Engineering liposomes for drug delivery: progress and problems", Trends Biotechnol 13, 527-37 (1995).
Gregoriadis and Allison, "Entrapment of proteins in liposomes prevents allergic reactions in pre-immunised mice", FEBS Lett 45:71-4 (1974).
Gregoriadis and Ryman, "Liposomes as carriers of enzymes or drugs: a new approach to the treatment of storage diseases", Biochrem. J., 124:58P (1971).
Gregoriadis, et al., "Improving the therapeutic efficacy of peptides and proteins: a role for polysialic acids", Intl, J. Pharm., 300:125-30 (2005).
Gregoriadis, "The carrier potential of liposomes in biology and medicine (second of two parts", N Engl J Med 295:765-70 (1976).
Guevremont, et al., "Comparison of cation-exchange and chelating cation-exchange resins for the concentration of saxitoxin", Analy. Chimica Acta., 255:163-68 (1991).
Haller, et al., "Differential neurotoxicity of tricyclic antidepressants and novel derivatives in vitro in a dorsal root ganglion cell culture model", Eur J Anaesthesiol., 24(8):702-708 (2007).
Harden, "Chronic neuropathic pain. Mechanisms, diagnosis and treatment", The Neurologist, 11(2):111-22 (2005).
Hoebeeck, et al., "Rapid detection of VHL exon deletions using real-time quantitative PCR", Lab. Invest., 85(1):24-33(2005).
Hu, "Interactions of Neosaxitoxin with the sodium channel of the frog sketletal muscle fber", J Gen Physiology, 97:561-78 (1991). vbTab.
Jia, et al., "Prolongation of sciatic nerve blockade by in situ cross-linked hyaluronic acid", Biomaterials, 25(19):4797-4804 (2004).
Kao, "Tetrodotoxin, saxitoxin and their significance in the study of excitation phenomena," Pharmacological Rev., 18(2):999-1049 (1966).
Kohane, et al., "A re-examination of tetrodotoxin for prolonged duration local anesthesia", Anesthesiology, 89:119-31 (1998a).
Kohane, et al., "Biocompatibility of lipid-protein-sugar particles containing bupivacaine in the epineurium", J Biomed Mater Res., 59(3):450-459 (2002).
Kohane, et al.,"Effects of adrenergic agonists and antagonists on tetrodotoxin-induced nerve block", Reg Anesth Pain Med, 26:239-45 (2001).
Kohane, et al., "Prolonged duration local anesthesia from tetrodotoxin-enhanced focal anesthetic microspheres", Pain,104(1-2):415-21 (2003).
Kohane, et al., "Sciatic nerve blockade in infant, adolescent, and adult rats: a comparison of ropivacaine with bupivacaine", Anesthesiology, 89:1199-1208 (1998b).
Kohane, et al., "The local anesthetic properties and toxicity of saxitonin homologues for rat sciatic nerve block in vivo", Reg Anesth Pain Med., 25:52-9 (2000).
Kohane, et al., "Vanilloid receptor agonists potentiate the in vivo local anesthetic activity of percutaneously injected site 1 sodium channel blockers", Anesthesiology, 90:524-34(1999).
Kushla, et al., "Noninvasive assessment of anesthetic activity of topical lidocaine formulations", J Pharm Sci, 82:1118-22 (1993).
Kuznicki, et al., "Structure of neosaxitoxin", Am Chem Soc., 0002-7863/7:6791-3 (1978).
Lagos, "The first evidence of paralytic shellfish toxins in the freshwater cyanobacteria cylindrospermopsis racivorski", Toxicon, 37:1359-73 (1999).
Llewellyn, "Saxitoxin, a toxic marine natural product that targets a multitude of receptors", Nat. Prod. Rep., 23:200-222 (2006).
Lim, et al. "The Quaternary Lidocaine Derivtive, QX-314, Produces Long-lasting Local Anesthesia in Animal Models In Vivo", Anesthesiology, 107:305-11 (2007).
Lirk, et al., "The neurotoxic effects of amitriptyline are mediated by apoptosis and are effectively blocked by inhibition of caspase activity", Anesth Analg., 102(6):1728-33 (2006).
Long, et al., "Cellular microcystin content in N-Limited Microcystis aerginosa can be predicted from growth rate", Appl. Enviro. Microbiol., 67(1):278-83 (2001).
Luo, et al., "Injury type-specific calcium channel alpha 2 delta-1 subunit up-regulation in rat neuropathic pain models correlates with antiallodynic effects of gabapentin", J Pharmacol Exp Ther., 303(3):1199-1205 (2002).
Malinovsky, et al., "A dose-response study of epidural liposomal bupivacaine in rabbits", J Control Release., 60(1):111-119 (1999).
Mandel and Lee, "Listeriolysin O-liposome-mediated cytosolic delivery of macromolecule antigen in vivo: enhancement of antigen-specific cytotoxic T lymphocyte frequency, activity, and tumor protection", Biochim Biophys Acta 1563:7-17 (2002).
Masters, et al., "Prolonged regional nerve blockade by controlled release of local anesthetic from a biodegradable polymer matrix" Anesthesiology, 79(2):340-346 (1993).
Mazur-Marzec, "Characterization of phycotoxins produced by cyanobacteria", Intl J Oceanography and Hydrobiology, XXXV (1):85-109 (2006).
McLure and Rubin , "Review of local anaesthetic agents", Minerva Anesthesiol., 71:59-74 (2005).
Mearow, et al., "Stress-mediated signaling in PC12 cells—the role of the small heat shock protein, Hsp27, and Akt in protecting cells from heat stress and nerve growth factor withdrawal", Journal of neurochemistry, 83(2):452-462 (2002).
Media recipes used in CMAR,CMAR Methods. Retrieved Aug. 2, 2008 http://www.marine.csiro.au/microalgae/methods/Media%20CMARC%20recipes.htm.
Middleton, "Mechanism of action of surfactants on water binding properties of isolated stratum corneum", J Soc Cosmet Chem. ,20:399-403 (1969).
Minko, et al., "New generation of liposomal drugs for cancer", Anticancer Agents Med Chem 6, 537-52 (2006).
Myers, et al., "Neurotoxicity of local anesthetics: altered perineurial permeability, edema, and nerve fiber injury", Anesthesiology, 64:29-35 (1986).
Nakagomi, et al,, "Expression of the activating transcription factor 3 prevents c-Jun N-terminal kinase-induced neuronal death by promoting heat shock protein 27 expression and Akt activation", J Neurosci., 23(12):5187-5196 (2003).
Newton, et al., "Dorsal root ganglion neurons show increased expression of the calcium channel alpha2delta-1 subunit following partial sciatic nerve injury", Brain Res Mol Brain Res., 95(1-2):1-8 (2001).
Nixdrof, "Phytoplankton assemblages and steady state in deep and shallow eutropic lakes—an approach to differentiate the habitat properties of Oscillatoriales", Hydrobiologia, 502:111-21 (2003).
Olivera, et al., "Diversity of Conus Neuropeptides," Science, 249:257-63, (1990).
Oshima, "Postcolumn derivatization liquid chromatographic method for paralytic shellfish toxins", J of AOAC Intl., 78(2):528-32 (1995).
Padera, et al., "Tetrodotoxin for prolonged local anesthesia with minimal myotoxicity", Muscle Nerve, 34:747-53 (2006).
Padera, et al., "Local myotoxicity from sustained release of bupivacaine from microparticles", Anesthesiology, 108(5):921-928 (2008).
Pere, et al., "Local myotoxicity of bupivacaine in rabbits after continuous supraclavicular brachial plexus block", Reg Anesth, 18(5):304-307 (1993).
Pomati, et al., "The purine degradation pathway: possible role in paralytic shellfish toxin metabolism in the *Cyanobacterium planktothrix* sp. FP1", Environ. Int., 27:463-470 (2001).
Pomati, et al., "Evidence for differences in the metabolism of saxitoxin and C1+2 toxins in the freshwater cyanobacterium Cylindrospermopsis raciborskii T3", Biochem.Biophys. Acta., 1674:60-67 (2004).

(56) References Cited

OTHER PUBLICATIONS

Ribaud, et al., "Organization of stratum corneum lipids in relation to permeability: influence of sodium lauryl sulfate and preheating", Pharm Res 11:1414-8 (1994).
Rodriguez-Navarro, et al., "Neosaxition as a local anesthetic", Anesthesiology, 106:339-45 (2007).
Rodriguez-Navarro, et al., "Potenriation of local anethetic activity of neosaxitoxin with bupivacaine or epinephrine developmenr of a long-acting pain blocker", Neurotox. Res., 16:408-15 (2009).
Rodriguez-Navarro, et al., "Comparison of neosaxitoxin versus bupivacaine via port infiltration for postoperarive analgesia following laparoscopic cholecystectomy", Reg. Anesth. Pain Med., 36:103-9 (2011).
Rositano, et al., Ozonation of nom and algal toxins in four treated waters, Wat. Rev., 35(1):23-32 (2001).
Ruetsch., et al., "From cocaine to ropivacaine: the history of local anesthetic drugs", Curr. Top. Med. Chem., 1:175-182 (2001).
Sagie and Kohane, "Prolonged sensory-selective neve blockade", Natl. Acad. Sci, 107(8):3740-5 (2010).
Sakura, et al., "Local anesthetic neurotoxicity does not result from blockade of voltage-gated sodium channels", Anesth Analg., 81:338-46 (1995).
Sapra, et al., "Ligand-targeted liposomes for cancer treatment", Curr. Drug Deliv., 2:369-81 (2005).
Sayfritz, et al., "Determination of paralytic shellfish poisoning toxins in Norwegian shellfish by liquid chromatography with fluorescence and tandem mass spectrometry detection", Toxicom, 52:330-40 (2008).
Schneider, et al., "A preferential inhibition of impulses in C-fibers of the rabbit vagus nerve by veratridine, an activator of sodium channels," Anesthesiology,74:270-81 (1991).
Scholz, "Mechanisms of (local) anaesthetics on voltage-gated sodium and other ion channels", Br J. Anaesth., 89:52-61 (2002).
Scurlock, et al. "Tetraethylammonium derivatives: Ulatralong-acting Local Anesthetics", Anesthesiology, 54:265-9 (1981).
Shankarappa, et al., "Lipsome-encapsulated saxitoxin in the trearment of nerve injury-induced chronic neuropathic pain", 41st annual meeting Society-for-neuroscience, Nov. 12-16, Washington DC (2011).
Shankarappa, et al., Prolonged nerve blockage delays the onset of neuropathic pain. PNAS, 109(43):17555-60 (2012b).
Shankarappa, et al., "Duration and local toxicity of sciatic nerve blockade with coinjected site 1 sodium-channel blockers and quaternary lidocaine derivatives", Reg. Anesthesia Pain Med., 37(5):483-9 (2012a).
Shimizu, "Biosynthesis of red tide toxins", Marine Toxins, 418:21-8 (1990).
Simons, et al., "Effect of chemical permeation enhancers on nerve blockade", Mol Pharmaceutics, 6:265-73 (2009).
Sleno, et al., "Gas-phase dissociation reactions of protonated saxitoxin and neosaxition", J am Soc Mass Spectrom, 15:462-77 (2004).
Scares, et al., "Neuronal and glial expression of the adhesion molecule TAG-1 is regulated after peripheral nerve lesion or central neurodegeneration of adult nervous system", Eur J Neurosci., 21(5):1169-1180 (2005).
Song, et al., "Axotomy-induced dopaminergic neurodegeneration is accompanied with c-Jun phosphorylation and activation transcription factor 3 expression", Exp Neurol., 209(1):268-278 (2008).
Soto, et al., "The effects of chloramphenicol, arginine and temperature on PST-production by Cylindrospermopsis raciborskii strain D9", Proceedings of the 12th Intl. Conf. on Harmful Algae, Copenhagen (2008).
Strichartz, "Structural determinanrs of affinity of saxitoxin for neuronal sodium channels", J Gen. Physiol., 84:281-305 (1984).
Szoka, et al., "Comparative properties and methods of preparation of lipid vesicles (liposomes)", Annual review of biophysics and bioengineering, 9:467-508 (1980).
Thalhammer, et al., "Neurologic evaluation of the rat during sciatic nerve block with lidocaine," Anesthesiology, 82(4):1013-25 (1995).
Tyagi, et al., "Urodynamic and immunohistochemical evaluation of intravesical capsaicin delivery using thermosensitive hydrogel and liposomes", J Urol 171:483-9 (2004).
Vandesompele, et al., "Accurate normalization of real-time quantitative RT-PCR data by geometric averaging of multiple internal control genes", Genome biology, 3(7):RESEARCH0034 (2002).
Wagner, et al., "Salitoxin and Procaine Act Independently on Separate Sites of the Sodium Channel," Pflugers Arch., 364:65-70 (1976).
Wall, et al., "Autonomy following peripheral nerve lesions: experimental anesthesia dolorosa", Pain., 7(2):103-111 (1979).
Wylie, et al., "Respiratory and neuromuscular effects of neosaxition in anesthetized sheep", Abstract for presentation at the ASA annual meeting, 3 pages, Oct. 2011.
Wylie, et al., "Respirarory, neuromuscular, and cardiovascular effects of neosaxitoxin in isoflurane-anesthetized sheep", Reg, Anes. Pain Med., 00:1-7 (2012).
Wu, et al., Lipid-based nanoparticulate drug delivry sysrems. In D Thassu (Ed.), Nanoparticulate Drug Delivery Systems, pp. 89-98 (2007).
Yahalom, et al., "Spinal anesthesia in infant rats: development of a model and assessment of neurologic outcomes", Anesthesiology, 114(6):1325-35 (2011).
Yamashita, et al., "A comparison of the neurotoxic effects on the spinal cord of tetracaine, lidocaine, bupivacaine, and ropivacaine administered intrathecally in rabbits", Anesth Analg, 97(2):512-519 (2003).
Zanen, et al., "The optimal particle size for parasympathicolytic aerosols in mild asthmatics", Int J Pharm., 114:111-5. (1995).
Zimmer, et al., "Cardiotoxic and neurotoxic effects after accidental intravascular bupivacaine administration. Therapy with lidocaine propofol and lipid emulsion", Anaesthesist, 56(5):449-453 (2007).
Zimmermann, "Ethical guidelines for investigations of experimental pain in conscious animals", Pain, 16(2):109-110 (1983).
Anonymous, "NCT1786655: Clinical Trials", Government Archives, retrieved from the internet: http://clinicaltrials.gov/archive/NTC01786655/2013_02_11, accessed Jun. 12, 2014.

* cited by examiner

NEOSAXITOXIN COMBINATION FORMULATIONS FOR PROLONGED LOCAL ANESTHESIA

CROSS REFERENCE TO RELATED APPLICATIONS

This application is a continuation of prior U.S. Ser. No. 14/216,252 filed Mar. 17, 2014, entitled "Neosaxitoxin Combination Formulations For Prolonged Local Anesthesia", by Charles Berde and Daniel S. Kohane, which claims priority to and benefit of U.S. Ser. No. 61/789,054 filed Mar. 15, 2013, entitled "Combinations of Neosaxitoxin with Bupivacaine and Epinephrine Increase Efficacy of Peripheral Nerve Block and Infiltration Local Anesthesia and Analgesia Without Increasing Toxicity", by Charles Berde, the teachings of which are incorporated herein by reference in their entirety.

FIELD OF THE INVENTION

This is generally in the field of improved nerve blocks and infiltration local anesthesia and analgesia with no increase in toxicity, specifically combinations of neosaxitoxin with bupivacaine, alone or in combination with epinephrine, in specific total and concentration dosages.

BACKGROUND OF THE INVENTION

A non-sustained release agent that reliably gives 6-12 hours of surgical-grade nerve block followed by up to approximately 48 h of lesser blockade and pain relief without additional treatment is desirable. The former period would be useful intra-operatively as well as in the immediately post-op period; the latter would provide decreasing analgesia and allow increasing use of the involved body part as healing progresses. Exparel™, the only prolonged duration local anesthetic on the market, provides unpredictable nerve blockade in humans that peaks at 24 h after injection and the anesthetic effect is inversely proportional to dose. Moreover it entails the use of a sustained release system and causes local tissue injury and inflammation.

Similar considerations relate to bupivacaine+dexamethasone microparticles, which could provide prolonged duration local anesthesia albeit with a sustained release system and with very severe tissue injury. The quaternary lidocaine derivative QX-314 could provide prolonged duration local anesthesia (approx. 24 h duration) but with very severe local tissue injury and systemic toxicity.

When amino-amide and amino-ester local anesthetics are given in overdose or via inadvertent intravascular injection, they generate cardiovascular toxicity that is notoriously refractory to resuscitation (Polaner et al. Ped Anes 2011; 21:737-742; Fisher, et al., *Can. J. Anaesth.,* 1997; 44: 592-598; Butterworth, *Reg. Anesth. Pain Med.,* 2010; 35:167-76). Bupivacaine cardiovascular toxicity is likely mediated by the cardiac sodium channel Nav1.5 which is relatively more resistant to binding and inactivation by site 1 sodium channel blockers (Clarkson, et al., *Anesthesiology,* 1985; 62:396-405).

The phycotoxins neosaxitoxin, saxitoxin and gonyaulatoxins are active compounds produced by harmful algae blooms of the genera *Alexandrium* sp., *Piridinium* sp., and *Gimnodinium* sp., (Lagos, N. Biol. Res., 31: 375-386 1998)). In the last 15 years, it has been demonstrated that these phycotoxins can also be produced by fresh water cyanobacteria such as photosynthetic blue-green algae, besides being produced by marine dinoflagellates.

Only four genera of cyanobacteria able to produce paralyzing phycotoxins have been identified, and each produces a different mixture of phycotoxins both in amounts and in types of phycotoxins produced, i.e. they produce different profiles of paralyzing phycotoxins (Lagos, et al., 1999, *TOXICON,* 37: 1359-1373 (1999). Pereira, et al., *TOXICON,* 38: 1689-1702 (2000).

The chemical structure of these phycotoxins has a general structure (I) and its particular structure is defined by the substituents R1 to R5 according to the following table:

(I)

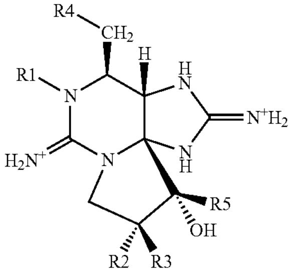

| Compound | R1 | R2 | R3 | R4 | R5 |
|---|---|---|---|---|---|
| Saxitoxin | H | H | H | $COONH_2$ | OH |
| Neosaxitoxin | OH | H | H | $COONH_2$ | OH |
| Gonyaulatoxin 1 | OH | H | $OSO^{-3}$ | $COONH_2$ | OH |
| Gonyaulatoxin 2 | H | H | $OSO^{-3}$ | $COONH_2$ | OH |
| Gonyaulatoxin 3 | OH | $OSO^{-3}$ | H | $COONH_2$ | OH |
| Gonyaulatoxin 4 | H | $OSO^{-3}$ | H | $COONH_2$ | OH |
| Gonyaulatoxin 5 | H | H | H | $COONHSO^{-3}$ | OH |

These paralyzing phycotoxins act as a specific blocker of the voltage-dependent sodium channels present in excitable cells (Kao, C. Y., *Pharm. Rev.,* 18: 997-1049 (1966)). Due to the inhibition of sodium channels, the transmission of a nervous impulse is blocked and the release of neurotransmitters is prevented at the level of the neuromotor junction, which prevents muscular contraction. Due to these physiological effects, these compounds are potentially useful in pharmacology when used as muscular activity inhibitors in pathologies associated with muscular hyperactivity, such as muscular spasms and focal dystonias, when applied locally in injectable form. Additionally, since a blockage of the nervous impulse at the transmission level is generated when these compounds are applied as a local infiltration, they are not only able to block the efferent neurotransmission pathways, but also block afferent pathways and cause an inhibition of the sensory pathways and generate an anesthetic effect when these compounds are locally injected. This is a surprising effect, since both effects are simultaneous, as described in U.S. Pat. No. 4,001,413.

As described in U.S. Pat. No. 6,326,020 by Kohane, et al., combinations of naturally occurring site 1 sodium channel blockers, such as tetrodotoxin (TTX), saxitoxin (STX), decarbamoyl saxitoxin, and neosaxitoxin, with other agents, have been developed to give long duration block with improved features, including safety and specificity. In one embodiment, duration of block is greatly prolonged by combining a toxin with a local anesthetic, vasoconstrictor, glucocorticoid, and/or adrenergic drugs, both alpha agonists (epinephrine, phenylephrine), and mixed central-peripheral alpha-2 agonists (clonidine), or other agents. Prolonged nerve block can be obtained using combinations of toxin with vanilloids. Dosage ranges based on studies with tetrodotoxin and saxitoxin were provided. However, it is now known that studies must be conducted with each toxin in order to predict the effective dosages, since dosages with one type of toxin are not predictive of efficacy with another type of toxin. As demonstrated in the following examples, it has also been discovered that one cannot extrapolate from rats or sheep to humans to determine safe and efficacious dosages with respect to these toxins.

Conventional local anesthetics are associated with local neurotoxicity in clinical doses and profound cardiovascular toxicity in overdose. While overall incidence is low, studies have also identified prolonged numbness and paresthesias as a complication of local and regional anesthesia with amide anesthetics. This has been associated with histological signs of chemical nerve injury (Myers, et al., *Anesthesiology,* 1986; 64:29-35; Kalichman, et al., *J. Pharm. Exper. Therapeutics,* 1989; 250(1):406-413). These risks for local neurotoxicity are likely to be further increased in the setting where prolonged pain relief is attempted via adminstration of conventional local anesthetics by controlled release delivery (Padera, et al., *Anesthesiology,* 2008; 108: 921-8; Kohane and Langer, *Chem. Sci.,* 2010; 1: 441-446) or local perineural infusions, particularly when higher concentrations or doses are used for longer periods of time. In equipotent intrathecally injected doses, site 1 sodium channel blockers cause longer duration of anesthesia with less histologic evidence of neurotoxicity compared to bupivacaine (Sakura, et al., *Anesth. Analg.,* 1995; 81:338-46). Overall, approaches to prolonged local anesthesia involving site 1 sodium channel blockers lower the risks of nerve injury compared to approaches involving prolonged or repeated administration of conventional amino-amides or amino-esters.

It is therefore an object of the present invention to provide specific combinations of neosaxitoxin with bupivacaine, optionally with epinephrine, to provide pain relief for up to two to three days following a single injection, which are both safe and efficacious in humans.

It is a further object of the present invention to provide formulations for providing safe and efficacious local anesthesia and analgesia in pediatric patients.

It is still another object of the present invention to provide formulations for treating indications requiring high, medium and low volumes of local anesthesia.

It is a further object of the present invention to provide formulations for treating indications requiring different rates of recovery from sensory or motor blockade due to local anesthesia.

SUMMARY OF THE INVENTION

Studies were conducted to identify dosages of neosaxitoxin ("NeoSTX") and bupivacaine, alone or in combination with epinephrine, to provide up to two to three days of pain relief. Studies using percutaneous blockade of the sciatic nerve in rats demonstrated that 1) Bupivacaine-NeoSTX combinations do not increase systemic toxicity compared to NeoSTX alone; 2) Bupivacaine-NeoSTX combinations produce more reliable blockade and longer duration blockade compared to NeoSTX alone; and 3) the three-way combination of NeoSTX-bupivacaine-epinephrine produces more prolonged local anesthesia than the two-way combination of NeoSTX-bupivacaine. Addition of epinephrine to this NeoSTX-bupivacaine combination dramatically prolongs the duration of complete blockade to a mechanical stimulus.

Studies in both rats and sheep showed that NeoSTX does not produce cardiotoxicity, even when injected intravenously. However, it is not possible to determine the efficacious dosages in humans, adult or pediatric, awake or non-awake, using animal studies due to limiting side effects determinable in humans and not animals.

These 2-way and 3-way combinations use additive or synergistic interactions to enhance efficacy, while the toxic effects of the combinations are less-than-additive, thus improving the overall margin of safety and efficacy. Based on these unexpected effects on efficacy, in the rat and human studies, the concentration of bupivacaine chosen, 0.2%, is lower than the standard commercial bupivacaine concentrations of 0.25%, 0.5% or 0.75%.

Human Phase 1 studies were conducted under an investigator-initiated IND with FDA and IRB approvals. The study demonstrated that combinations of NeoSTX-bupivacaine, alone or in combination with epinephrine, in different ratios for different clinical indications, provide a clinically important improvement in efficacy, duration of pain relief, and safety for local anesthesia compared to the standard, bupivacaine. The results demonstrated:

1. NeoSTX-bupivacaine 0.2% combinations, even with NeoSTX doses as low as 5-10 mcg (concentrations from 0.5-1 mcg/ml), and even without epinephrine, prolongs block relative to the standard, bupivacaine, by roughly 4-fold (FIGS. 7 and 8).
2. NeoSTX alone, i.e. dissolved in normal saline solution, is ineffective and inconsistent in tolerable doses, so the human data strongly support the requirement for the NeoSTX-bupivacaine combination (FIGS. 7 and 8)
3. Epinephrine reduces systemic symptoms, thereby broadening the safety margin, prolongs the duration of dense blockade (suitable for surgical anesthesia) and prolongs the analgesic duration further (e.g. from 48-72 hours), (FIG. 8). This permits dosing in high volume applications that have recently become very widely used for wound infiltration for hip and knee surgery (more than 100 mls are routine) and large abdominal surgeries.
4. Side effects (tingling, vomiting, nausea) limit the tolerable dosage of NeoSTX-bupivacaine in awake patients to less than 40 mcg NeoSTX, though higher doses should be safe in patients under general anesthesia. Note these limiting side-effects were seen with NeoSTX-saline and NeoSTX-bupivacaine, not with NeoSTX-bupivacaine-epinephrine.

Specific volumes and concentration of the components that will improve safety, tolerability and efficacy in specific clinical situations have now been identified. These discoveries led to studies to develop the following combination dosage formulations:

A dosage formulation for high volume use of 35-120 ml for adult humans and 0.5-1.8 ml/kg for children, includes as the active agents a three-way combination of bupivacaine in a concentration range between 0.1% (1 mg/ml) and 0.25% (2.5 mg/ml), giving a total systemic bupivacaine dose of no more than 225 mg in adults or 2.5 mg/kg in children; NeoSTX in a concentration range from 0.1 mcg/ml-1 mcg/ml, giving a total systemic dose of 3.5-100 mcg in adults or 0.05-1.5 mcg/kg in children, and Epinephrine in a concentration range between 2 mcg/ml (1:500,000 in common terminology) and 10 mcg/ml (1:100,000). Common use of this formulation would be for infiltration of three or four layers of a large surgical wound for a full-length open laparotomy, thoraco-abdominal incision, or flank incision.

Some of these operations include: Cesarian delivery, open hysterectomy, esophago-gastrectomy, nephrectomy, or large abdominal cancer surgeries such as colectomies. Wound infiltration for total hip replacement (hip arthroplasty) and total knee replacement (knee arthroplasty) would also be ideal uses for these formulations.

Dosages formulation for medium volume use of 15 to 50 ml, includes as the active agents a combination of Bupivacaine in a concentration range of 0.125%-0.3% (1.25-3 mg/ml), giving a systemic dose in adults of no more than 100 mg (no more than 2 mg/kg in children), NeoSTX in a concentration range from 0.2-2 mcg/ml, giving a systemic dose in adults of 7-150 mcg (0.1-1.5 mcg/kg in children), and Epinephrine in a concentration range from 0-10 mcg/ml (≤1:100,000).

Many of the intended uses for moderate volume formulations involve both peripheral nerve blocks or plexus blocks (perineural injection) as well as infiltration (injection along the layers of a surgical wound). Uses of this formulation include shoulder, arm, or hand surgery, infiltration or ilio-inguinal/ilio-hypogastric blocks for inguinal hernia repair, penile block for hypospadias repair, femoral block for total knee replacement or anterior cruciate ligament repair, intercostal nerve blocks for open chest surgery, or femoral and sciatic nerve blocks for leg amputation. For hip surgery, this could involve lumbar plexus block and lower volume sciatic block. This formulation could also be used for nerve blocks (femoral and sciatic, lumbar plexus and sciatic) for hip or knee joint for joint replacement surgery.

For some of these medium volume uses, particularly with peripheral nerve blocks and plexus blocks, a high priority is to provide three features:

i. anesthesia (near-complete insensitivity) for surgery for periods of 3-12 hours, ii. analgesia (prolonged pain relief) after surgery for periods of at least 24 hours, while ensuring, iii. recovery from motor block to permit some strength in limb movement by a time frame of 24-48 hours.

For peripheral nerve blocks and plexus blocks with motor effects on arms and legs, based on the requirement for recovery from motor block from 24-48 hours, formulations with NeoSTX-bupivacaine without epinephrine are likely to be ideal, as detailed in the following tables.

A dosage formulation for low volume, long duration, includes as the active agents a combination of Bupivacaine in a concentration of 0.25%-0.5% (2.5-5 mg/ml), wherein 5-15 ml dosing gives a systemic bupivacaine dose in adults of no more than 75 mg, NeoSTX in a concentration range from 0.5-5 mcg/ml, wherein 5-15 ml dosing gives a systemic dose in adults of 5-75 mcg, and Epinephrine in a concentration range from 2.5-10 mcg/ml (1:500,000-1:100,000). An example is lumbar sympathetic blockade for complex regional pain syndrome/reflex sympathetic dystrophy or vascular insufficiency of the leg or for celiac plexus blockade for pancreatitis or cancer of the pancreas.

It is desirable to have this type of block last as long as possible, since when performed using fluoroscopic guidance in small volumes, there is very little sensory or motor block. Therefore, relatively high concentrations of all three components should be used for this application to achieve durations of sympathetic blockade and increased local blood flow for at least 3-4 days, and possibly longer. Other applications that can involve this low volume, long duration use would include sciatic nerve blockade of prolonged duration where rapid motor recovery is not an issue, as for a lower leg amputation.

BRIEF DESCRIPTION OF THE DRAWINGS

FIGS. 1A-1F are graphs of the intensity of blockade after sciatic nerve injection in rats as described in Example 1 at 15 minutes for Hotplate, EPT, and Von Frey testing in the injected hindlimb (FIGS. 1A-1C) and the contralateral hindlimb (FIG. 1D-1F), comparing limb withdrawal latency (seconds) (1A, 1D); extensor postural thrust (g) (1B, 1E), and force for limb withdrawal (g) (1C, 1F).

FIGS. 2A-2F are graphs showing the duration of blockade after sciatic injection in rats as described in Example 1 for Hotplate recovery (hours) (2A, 2D), EPT recovery (hours) (2B, 2E), and Von Frey recovery (hours) (2C, 2E) testing in the injected hindlimb (2A-2C) and the contralateral hindlimb (2D-2F).

FIG. 3 is a graph of LD50 (in micrograms) curves of 2 formulations of NeoSTX, Neo 4 (lines on left of graph) and Neo 5 (lines on right of graph), with and without bupivacaine, based on rat data.

FIGS. 4A-4C are graphs of Von Frey testing in rats over time for 0.2% bupivacaine (FIG. 4A), 0.2% bupivacaine plus 3 NeoSTX/kg (FIG. 4B), and 0.2% bupivacaine plus 3 μg NeoSTX/kg plus 5 epinephrine/kg (FIG. 4C).

FIGS. 5A and 5B are graphs of the grams mechanical force application in the Von Frey test over time in hours to the treated leg for 3.5 mcg NeoSTX (triangle) as compared to control (circle) (FIG. 5A) and as a function of 0.2% bupivacaine (circle), 0.2% bupivacaine and 3 mcg NeoSTX (square) or 0.2% bupivacain 3 mcg NeoSTX 5 mcg epinephrine/ml (triangle) (FIG. 5B). All three formulations produce rapid onset of dense mechanical sensory block. The graphs show that addition of NeoSTX 3 mcg/kg to Bupivacaine 0.2% produces 4-fold prolongation of full blockade (4 hours versus 1 hour) and 6-fold prolongation of half-maximal block (12 hours versus 2 hours). The results showed that addition of Epinephrine 5 mcg/kg to Bupivacaine 0.2%+NeoSTX 3 mcg/kg results in an additional 6-fold prolongation of full block (24 hours versus 4 hours) and an additional 2.5-fold prolongation of half-maximal block (30 hours versus 12 hours) compared to Bupivacaine 0.2%+NeoSTX 3 mcg/kg. Compared to the current standard, bupivacaine, the 3-way combination of Bupivacaine-NeoSTX-Epinephrine results in 24-fold prolongation of full block and 15-fold prolongation of half-maximal block.

FIG. 6A is a graph of the percentage of subjects having any systemic symptoms: tingling, numbness, dizziness, nausea or vomiting at any time point following administration of 0, 5, 10, 15, 20, 30 or 40 mcg NeoSTX-bupivacaine-epinephrine. Nausea was observed in 80% of subjects at 40 mcg NeoSTX. The graph shows that the occurrence of systemic symptoms of any time point score for NeoSTX-bupivacaine-epinephrine combination at NeoSTX doses or 10 mcg or 30 mct were not elevated above placebo. FIG. 6B is a graph of the percentage of subjects having clinically significant systemic symptoms, i.e. scores of greater than 3 on a 0-10 scale for 30 minutes or longer. FIG. 6B shows that there were no scores above zero for NeoSTX-bupivacaine-epinephrine subjects receiving doses of 10 mcg or 30 mcg.

FIGS. 7 A, B, and C are from the Phase 1 Human Study showing that addition of Epinephrine intensifies and prolongs block from NeoSTX Bupivacaine combinations. FIGS. 7A, 7B, and 7C are graphs of the threshold measurement of dense and partial blockade, mechanical detection (FIG. 7A), mechanical pain (FIG. 7B) and cool detection (FIG. 7C) for NeoSTX, NeoSTX+bupivacaine, NeoSTX+bupivacaine+epinephrine, compared to placebo and controls (no NeoSTX), over time in hours. The results demonstrate that Bupivacaine 0.2% gives dense block for no more than 6 hours, and partial analgesia between 6-12 hours. NeoSTX 10 mcg in saline gives highly variable and short-duration block. NeoSTX 10 mcg in bupivacaine 0.2% gives dense block for roughly 12 hours and degrees of analgesia over 24-72 hours. NeoSTX 10 mcg in bupivacaine 0.2% with epinephrine 5 mcg/ml gives dense block for 24 hours and degrees of analgesia over 48-72 hours.

FIGS. 8A, B and C are from the Phase 1 Human Study showing that NeoSTX-Bupivacaine combinations prolong block relative to bupivacaine alone in doses as low as 5 mcg. FIGS. 8A-C show graphs of measurement of dense and partial block of mechanical (FIG. 8A) and thermal (FIGS. 8B, 8C) detection for bupivacaine, NeoSTX-bupivacaine, and NeoSTX-bupivacaine-epinephrine at a NeoSTX dose of 10 mcg. The results show NeoSTX—Bupivacaine 0.2% combinations, in all NeoSTX doses ranging from 5 mcg to 40 mcg, produce dense block of multiple sensory modalities for at least 12 hours, analgesia for periods of 24-72 hours, and reliable recovery from dense mechanical block by 48 hours, as required for uses in peripheral blocks of nerves affecting motor function in the arms and legs.

DETAILED DESCRIPTION OF THE INVENTION

Figure 1A:
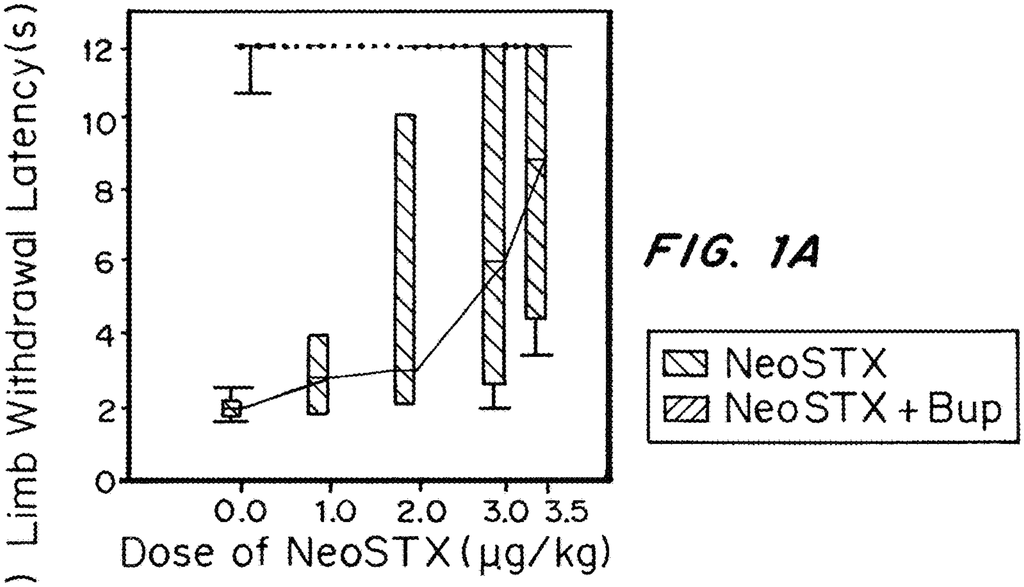
FIGS. 1A-1F show the rat dose-response for sciatic nerve blockade intensity at 15 minutes (peak effect) with NeoSTX in saline and NeoSTX-bupivacaine.
Figure 1B:
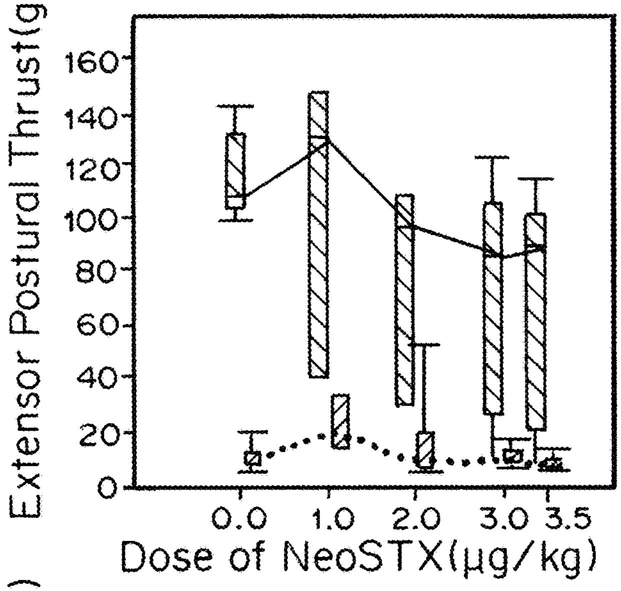
Figure 1C:
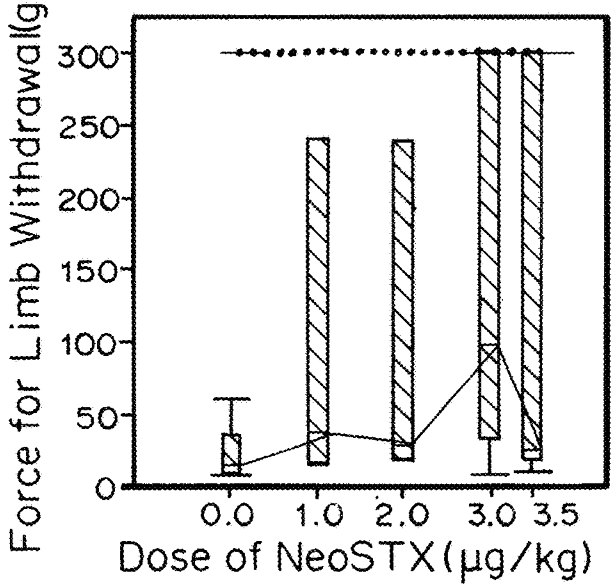
Figure 1D:
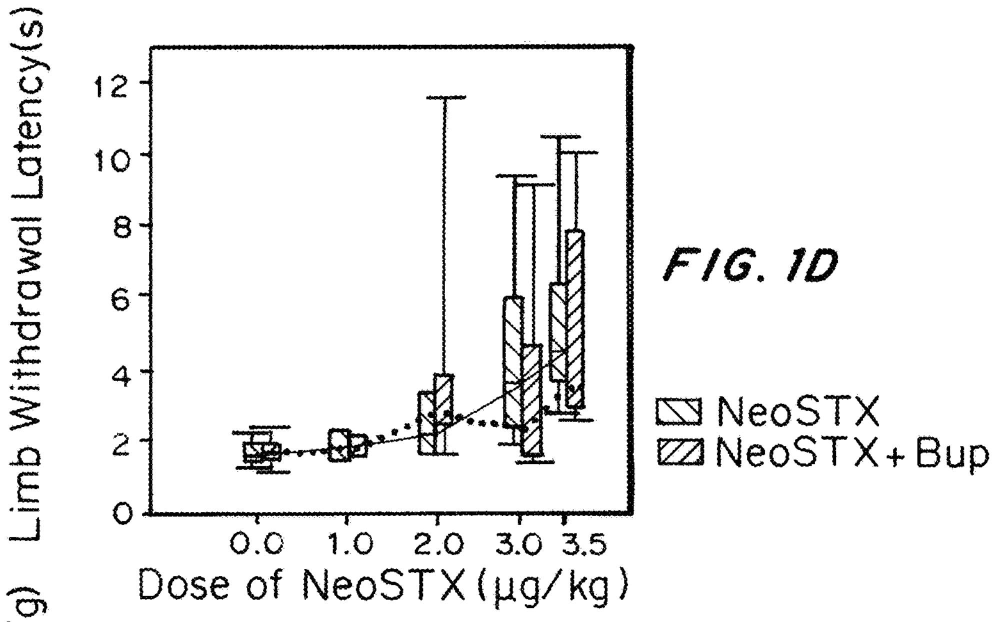
Figure 1E:
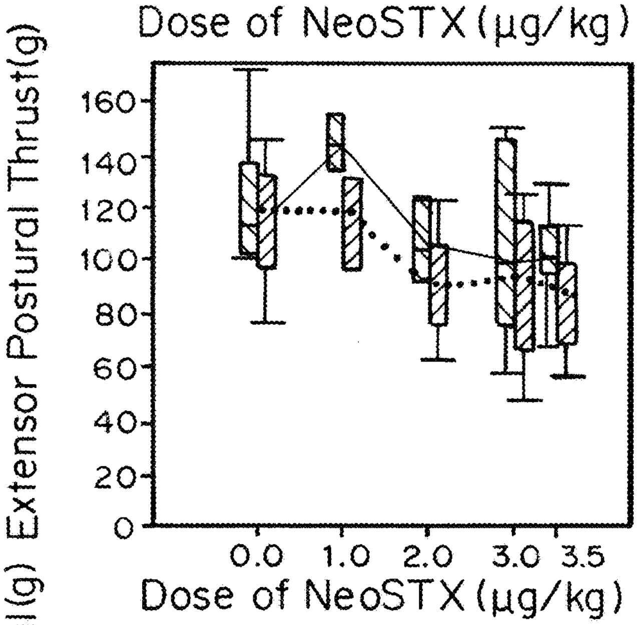
Figure 1F:
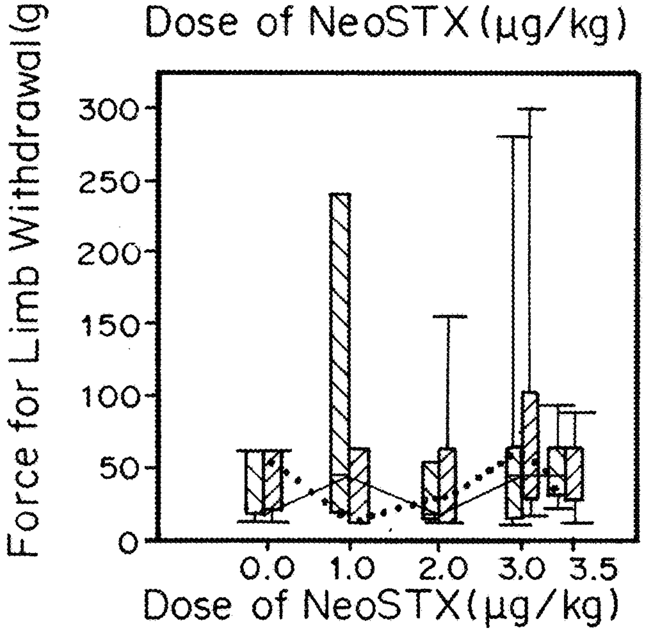

The safety benefits of reducing bupivacaine dosing with NeoSTX are important for patients at all ages, but especially so for children. Epidemiologic data from prospective registries indicates that younger children are at increased risk compared to adults for local anesthetic systemic reactions. Local anesthetics and regional anesthesia are being used increasingly to provide pain relief after surgery in infants and children. The greater safety margin afforded by these combinations has unique use in pediatrics. The optimal, preferred, and broad range doses, volumes and concentrations, for pediatric patients, for different indications, were derived based on considerations related to the physicochemical properties of NeoSTX and how sizes of body compartments and volumes of distribution scale with body weight in children and older infants.

Definitions

Analgesia refers to insensibility to pain without loss of consciousness.

Anesthetic refers to a loss of sensation (local; not causing loss of conscioiness; systemic, with loss of consciousness) and usually of consciousness without loss of vital functions.

Vasoconstrictor is an agent narrowing of the lumen of blood vessels especially as a result of vasomotor action.

Infiltration refers to injection into multiple layers or areas of tissue.

Injection refers to injection into a single point in tissue or lumen.

Nerve block refers to local anesthesia produced by interruption of the flow of impulses along a nerve trunk.

Minimum effective concentration ("MEC") is the lowest local concentration of one or more drugs in a given location sufficient to provide pain relief.

II. Compositions

A. Site 1 Sodium Channel Blockers

Site 1 blockers are a family of molecules long recognized for their potent and specific blockade of voltage gated sodium channels. Site I sodium channel blockers include tetrodotoxin (TTX), saxitoxin (STX), decarbamoyl saxitoxin, neosaxitoxin, and the gonyautoxins (referred to jointly herein as "toxins"). Tetrodotoxins are obtained from the ovaries and eggs of several species of puffer fish and certain species of California newts. Chemically, it is an amino perhydroquinaoline. See Pharmacological Reviews, Vol. 18 No. 2, pp. 997-1049. Tetrodotoxin alone is too toxic to be used as an anesthetic. Combinations of tetrodotoxin with bupivacaine produced long duration sciatic nerve blockade in rats without increased systemic toxicity compared to tetrodotoxin alone (Kohane, et al., *Anesthesiology,* 1998:119-131). Although the most widely known site 1 toxin, tetrodotoxin, is effective as an anesthetic, it is expensive for clinical use since it must come from the puffer fish; when the endo-symbiotic bacteria that makes TTX is grown ex vivo, its production of TTX diminishes.

Saxitoxin was first extracted from the Alaska butterclam, *Saxidomus gigantcus*, where it is present in algae of the genus Gonyaulax. The reported chemical formula is $C_{10}$ $H_{15}$ $N_7$ $O_3$0.2HCl. It is believed the toxin has a perhydropurine nucleus in which are incorporated two guanidinium moieties. Saxitoxin is also too toxic to be used alone as a local anesthetic.

Saxitoxin and its derivatives can be produced in bioreactors from algae. The two derivatives, neosaxitoxin (NeoSTX) and decarbamoyl saxitoxin, have advantages in terms of the production process and potency. A study examined rat sciatic nerve blockade with several members of the saxitoxin series, including NeoSTX (Kohane, et al., *Reg. Anesth. Pain Med.,* 2000; 25:52-9). Saxitoxin and these two derivatives all give markedly synergistic block and prolonged block (1-2 days in rat sciatic nerve in vivo) when combined with bupivacaine or epinephrine.

Neosaxitoxin and decarbamoyl saxitoxin are potentially more potent and may have advantages over saxitoxin in formulation. Neosaxitoxin (NeoSTX) is under clinical development as a prolonged duration local anesthetic (Rodriguez-Navarro, et al., *Anesthesiology,* 2007; 106:339-45; Rodriguez-Navarro, et al., *Neurotox. Res.,* 2009; 16:408-15; Rodriguez-Navarro, et al., *Reg. Anesth. Pain Med.,* 2011; 36:103-9). A Phase 1 study of subcutaneous infiltration in human volunteers showed that NeoSTX caused effective cutaneous hypoesthesia (Rodriguez-Navarro, et al., *Anesthesiology,* 2007; 106:339-45) and a second Phase 1 study showed that combination with bupivacaine resulted in more prolonged analgesia compared to NeoSTX or bupivacaine alone (Rodriguez-Navarro, et al., *Neurotox. Res.,* 2009; 16:408-15).

The preferred source of site I sodium channel blocker is the neosaxitoxin produced by *Proteus*, Chile.

B. Local Anesthetics

As used herein, the term "local anesthetic" means a drug which provides local numbness or pain relief. Classes of local anesthetics which can be utilized include the aminoacylanilide compounds such as lidocaine, prilocaine, bupivacaine, mepivacaine and related local anesthetic compounds having various substituents on the ring system or amine nitrogen; the aminoalkyl benzoate compounds, such as procaine, chloroprocaine, propoxycaine, hexylcaine, tetracaine, cyclomethycaine, benoxinate, butacaine, proparacaine, and related local anesthetic compounds; cocaine and related local anesthetic compounds; amino carbonate compounds such as diperodon and related local anesthetic compounds; N-phenylamidine compounds such as phenacaine and related anesthetic compounds; N-aminoalkyl amid compounds such as dibucaine and related local anesthetic compounds; aminoketone compounds such as falicaine, dyclonine and related local anesthetic compounds; and amino ether compounds such as pramoxine, dimethisoquien, and related local anesthetic compounds. The preferred local anesthetics are amino-amides and amino esters, with the most preferred being bupivacaine, the levoenantiomer of bupivacaine being preferred where vasoconstrictor activity of the local anesthetic is desirable, tetracaine, and ropivacaine, which is slightly more sensory selective.

These drugs average six to ten hours of pain relief when given in different sites and for different types of surgery. For many types of surgery, it would be preferable to have durations of pain relief that last two or three days. The preferred local anesthetics for use in combination with NeoSTX are bupivacaine, ropivacaine, tetracaine and levobupivacaine. Bupivacaine is a particularly long acting and potent local anesthetic. Its other advantages include sufficient sensory anesthesia without only partial motor blockade, and wide availability.

C. Vasoconstrictors

Vasoconstrictors which are useful are those acting locally to restrict blood flow, and thereby retain the injected drugs in the region in which they are administered. This has the effect of substantially decreasing systemic toxicity. Preferred vasoconstrictors are those acting on alpha adrenergic receptors, such as epinephrine and phenylepinephrine. Other drugs and dyes vasoconstrict as a side-effect, such as bupivacaine and levobupivacaine.

D. Excipients and Preservatives

The formulations may also contain preservatives, pH adjusting agents, antioxidants, and isotonicity agents.

In the preferred embodiment the anesthetic is formulated in saline, or an acidic buffered solution, optionally containing a preservative. Local or sustained release carriers may be utilized, but are not preferred.

E. Dosage Units

In preferred embodiments, the NeoSTX, bupivacaine and optionally epinephrine are provided in vials in an aqueous solution. Depending on the type of formulation, as outlined previously and below, the vial sizes may range from 15-40 mls, and 1-3 vials may be used for a single patient in different situations. In another embodiment, the NeoSTX, local anesthetic, and optionally vasoconstrictor, are provided in one or more vials, optionally lyophilized, then rehydrated and combined prior to use. For this second embodiment, preferred vial sizes could range from 5-40 mls.

III. Formulations and Dosages

Animal and human studies are required to determine effective dosages and volumes for treatment of humans. For example, the rank order of potencies of site 1 sodium channel blockers from in vitro physiology experiments did not predict the rank order of potency of those compounds in vivo (Kohane, et al., *Reg. Anesth. Pain Med.,* 2000; 25: 52-9).

The following principles impose limits on local anesthetic doses, volumes and concentrations.

Different clinical situations place different demands on local anesthetic safety and efficacy.

Systemic safety determines the upper limit on the total dose (mg or mg/kg) of bupivacaine, NeoSTX, or other local anesthetics. There are small differences in total permissible dose based on the time course of uptake, vascularity, etc., but overall each local anesthetic has a maximum permissible total dose. As described herein, inclusion of epinephrine along with NeoSTX and bupivacaine increases efficacy and systemic safety, permitting larger doses or larger volumes and providing longer duration of pain relief. However, there are some locations in the body where epinephrine must be avoided due to excessive vasoconstriction. These include injections around the fingers and toes, and around the penis. Therefore, for different clinical uses, it is important to develop formulations both with and without epinephrine.

In any localized region of the body, a sufficient local tissue concentration of local anesthetics is required to block afferent transmission. The lowest local concentration of one or more drugs in a given location sufficient to provide pain relief is called the "minimum effective concentration" or MEC.

Thus, clinical situations that require infiltration into large tissue volumes require larger total volumes of local anesthetic at or above MEC than clinical situations that involve smaller tissue volumes. If the MEC is similar in different locations, then larger tissue volumes require a larger total dose than small tissue volumes.

For NeoSTX in saline and NeoSTX-bupivacaine-combinations in the Phase 1 human clinical trial, it was unexpected that systemic symptoms, including mild tingling and/or numbness of the fingers, lips and tongue occurred at doses of NeoSTX as small as 10 mcg total. These symptoms were mild at doses from 10-15 mcg, but increased in severity and were accompanied by transient nausea as doses were increased to 40 mcg. These symptoms were unexpected, because tingling and nausea were not knowable from non-human data. These human studies also showed that addition of epinephrine to NeoSTX-bupivacaine dramatically diminished the incidence of these symptoms in the NeoSTX dose range from 10-30 mcg (see FIG. 6). Therefore, there would be no way to know from previous data that epinephrine is needed at those concentrations to prevent tingling and nausea. In the human Phase 1 trial, epinephrine also dramatically increases the duration of block from NeoSTX+BPV.

In some clinical settings, it is important not to give large volumes (i.e. greater than 20 mls) of local anesthetic, in order to prevent spread of numbness or weakness to other locations in the body where these effects are undesirable or even dangerous. For example, injection of volumes greater than 20 ml for interscalene block of the brachial plexus, as used for shoulder surgery, increases the risk of spillover to the nearby nerves in the neck innervating the larynx, creating hoarse voice and risk for aspiration of liquids into the trachea. Similarly, volumes greater than 20 ml for lumbar sympathetic blockade increase the risk of spillover to the somatic nerves, with an associated risk for temporary leg weakness due to numbing the nerves to the major muscles of the leg. In other settings, unless very large volumes are used, some tissues will not be covered, and the result will be inadequate pain relief. Examples of these are cited below.

Human clinical trials have uncovered specific dosing considerations that were not predictable based on what was previously known regarding site 1 sodium channel blockers. Some of these are contrary to current conventional wisdom and clinical practice in local/regional local anesthesia. These considerations further impact the specific formulations that could be used safely in humans, in a manner that was not anticipated.

In rats, detectable nerve blockade begins at greater than 30 μM in 0.1 mL of injectate (Kohane, et al., *RAPM,* 25(1):1-107 (2000)), which corresponds to a dose of approximately 1 μg in a 350 g rat, which would be a dose of approximately 270 μg in a 70 kg human. As described in Example 1 and in additional studies, the dose response was determined in rats for local anesthesia using NeoSTX in saline, NeoSTX-bupivacaine, and NeoSTX-bupivacaine-epinephrine (see FIGS. 1, 2, 4, and 5). The bupivacaine concentration of 0.2% was the same for both rat and human studies. In rats, NeoSTX-bupivacaine combinations gave inconsistent or statistically insignificant prolongation of blockade compared to bupivacaine alone at NeoSTX doses of 2 mcg/kg, and reliable and robust prolongation was achieved only at NeoSTX doses of at least 3 mcg/kg. These studies were performed using an injection volume of 0.3 ml. Based on the rats' weights (approximately 250 gm), for these injections, NeoSTX doses of 3 mcg/kg correspond to NeoSTX concentrations in the injectates of 2.5 mcg/ml.

In contrast, in the human phase 1 trial, using NeoSTX-bupivacaine combinations, it was found that NeoSTX doses as low as 5 mcg (roughly 0.07 mcg/kg for these adult humans) gave excellent, i.e. 4-fold, prolongation of block compared to bupivacaine alone (FIG. 7), For an injection volume of 10 mls, this indicates a very strong block-prolonging effect for NeoSTX in NeoSTX-bupivacaine combinations in humans using a NeoSTX concentration of 5 mcg/10 mls, i.e. 0.5 mcg/ml.

Thus, NeoSTX in humans produces reliable block prolongation in NeoSTX-bupivacaine combinations at a weight-scaled NeoSTX dose at least 40-fold lower and at a NeoSTX concentration at least 5-fold lower than the corresponding effective NeoSTX weight-scaled doses and concentrations found in rats. The schedule for drug dosing and consequently the specific ranges of concentrations claimed for specific types of surgeries could not be derived from prior art because animals cannot be interrogated as to symptoms that do not elicit fairly significant toxicity. Specifically, it was found in human studies of NeoSTX that systemic symptoms including tingling, numbness of lips, fingers and tongue, and eventually nausea occurs at a weight-scaled dosage (15-40 mcg, or roughly 0.2-0.6 mcg/kg) far below that used in the rat studies (2-5 mcg/kg), see FIGS. 1-5, tingling, numbness and nausea are found both with impending toxicity from existing local anesthetics and from paralytic shellfish poisoning.

In summary:

The occurrence of these symptoms at these low doses was not anticipated by previous rat or human studies using NeoSTX.

For NeoSTX, symptoms occur far below doses that produce measurable physiologic effects such as weakness or impaired respiratory measures. These symptoms limit maximum doses of NeoSTX-bupivacaine in awake subjects more than in anesthetized subjects.

NeoSTX's symptoms imply less risk than when similar symptoms occur for excessive dosing of bupivacaine. If bupivacaine makes one tingle, odds are that one will soon either have a seizure, arrhythmia or cardiac arrest. This is not the case for NeoSTX.

Epinephrine dramatically reduces the severity of these symptoms, permitting tolerability of higher NeoSTX doses in these 3-way combinations compared to the 2-way combinations.

The schedule for drug dosing and consequently the specific ranges of concentrations claimed for specific types of surgeries is contrary to what is practiced world-wide in dosing local anesthetics. Systemic toxicity is rarely a limiting feature in using conventional local anesthetics, so adjustment of concentration to account for volume of injectate is not necessary. The use of NeoSTX and similar compounds necessitates a different approach, where a change in the composition of the drug solution itself is required Formulations optimized for different types of clinical situations have been developed.

"High Volume Infiltration Analgesia".

A dosage formulation for high volume use of 35-120 ml for adult humans and 0.5-1.8 ml/kg for children, includes as the active agents a three-way combination of bupivacaine in a concentration range between 0.1% (1 mg/ml) and 0.25% (2.5 mg/ml), giving a total systemic bupivacaine dose of no more than 225 mg in adults or 2.5 mg/kg in children; NeoSTX in a concentration range from 0.1 mcg/ml-1 mcg/ml, giving a total systemic dose of 3.5-100 mcg in adults or 0.05-1.5 mcg/kg in children, and Epinephrine in a concentration range between 2 mcg/ml (1:500,000 in common terminology) and 10 mcg/ml (1:100,000). Common use of this formulation would be for infiltration of three or four layers of a large surgical wound for a full-length open laparotomy, thoraco-abdominal incision, or flank incision. Some of these operations include: Cesarian delivery, open hysterectomy, esophago-gastrectomy, nephrectomy, or large abdominal cancer surgeries such as colectomies. Wound infiltration for total hip replacement (hip arthroplasty) and total knee replacement (knee arthroplasty) would also be ideal uses for these formulations. Common use of this formulation is for infiltration of three or four layers of the surgical wound for a full-length open laparotomy, thoraco-abdominal incision, or flank incision.

TABLE 1

| Large Volume Formulations (Adults) | | | |
|---|---|---|---|
| | Optimal | Preferred | Broader Range |
| Volumes | 70 ml | 50-100 ml | 35-120 ml |
| NeoSTX Concentrations | 0.3 mcg/ml | 0.2-0.4 mcg/ml | 0.1-0.8 Mcg/ml |
| Total NeoSTX Doses | 21 mcg | 10-40 mcg | 10-100 mcg |
| Bupivacaine Concentration | 0.2% (2 mg/ml) | 0.15-0.25% (1.5-2.5 mg/ml) | 0.1-0.3% (1-3 mg/ml) |
| Epinephrine Concentration | 5 mcg/ml | 2.5-7.5 mcg/ml | 2-10 mcg/ml |
| Typical Clinical Uses | Infiltration for large abdominal surgeries, including Cesarian delivery, hysterectomy and colectomy<br>Infiltration for hip and knee replacements,<br>Nerve blocks of the chest wall (paravertebral blocks for chest surgery and upper abdominal surgery) and abdominal wall (transversus abdominis plane blocks for abdominal surgery) | | |

TABLE 2

| Large Volume Formulations (Children) (All listings of "/kg" refer to scaling by the child's body weight) | | | |
|---|---|---|---|
| | Optimal | Preferred | Broader Range |
| Volumes | 1 ml/kg | 0.7-1.3 ml/kg | 0.5-2 ml/kg |
| NeoSTX Concentrations | 0.3 mcg/ml | 0.2-0.4 mcg/ml | 0.1-0.8 Mcg/ml |
| Total NeoSTX Doses | 0.3 mcg/kg | 0.2-0.4 mcg/kg | 0.1-1.5 mcg/kg |
| Bupivacaine Concentration | 0.2% (2 mg/ml) | 0.15-0.25% (1.5-2.5 mg/ml) | 0.1-0.3% (1-3 mg/ml) |
| Epinephrine Concentration | 5 mcg/ml | 2.5-7.5 mcg/ml | 1-10 mcg/ml |
| Typical Clinical Uses | Infiltration for large abdominal surgeries, including cancer surgeries and surgery for congenital anomalies<br>Infiltration for congenital hip repairs,<br>Nerve blocks of the chest wall (paravertebral blocks for chest surgery and upper abdominal surgery) and abdominal wall (transversus abdominis plane blocks for abdominal surgery) | | |

"Medium Volume, Intermediate Duration".

These uses involve a total volume of roughly 15-40 ml in adults or 0.2-0.6 ml/kg in children. In these applications, volumes must be kept comparatively low to prevent spillover to unwanted targets. For example, for shoulder surgery, interscalene block of the brachial plexus is commonly used. Ultrasound guidance is used for precise needle placement, and the total volume is limited to prevent spillover to unwanted targets, such as the recurrent laryngeal nerve (which affects the functioning of the larynx). Currently available blocks typically last 10 hours, and rarely up to 15-18 hours. This often means that blocks last until nighttime, and patients have severe pain the first postoperative night.

In this regimen, it is desirable to have blocks reliably producing pain relief for at least 24 hours (i.e. to get through the first night), and up to 48-72 hours, but the dense motor block and light-touch components of the block should diminish by around 24 hours, so that the patient has greater mobility of the arm and hand (for brachial plexus block) or of the leg (for femoral, lumbar plexus, or sciatic blocks) by the day after surgery.

Dosages formulation for medium volume use of 15 to 50 ml, includes as the active agents a combination of Bupivacaine in a concentration range of 0.125%-0.3% (1.25-3 mg/ml), giving a systemic dose in adults of no more than 150 mg (no more than 2 mg/kg in children), NeoSTX in a concentration range from 0.2-2 mcg/ml, giving a systemic dose in adults of 7-100 mcg (0.1-1.5 mcg/kg in children), and Epinephrine in a concentration range from 0-10 mcg/ml (≤1:100,000).

Many of the intended uses for moderate volume formulations involve both peripheral nerve blocks or plexus blocks (perineural injection) as well as infiltration (injection along the layers of a surgical wound). Uses of this formulation include shoulder, hand or arm surgery, infiltration or ilio-inguinal/ilio-hypogastric blocks for inguinal hernia repair, penile block for hypospadias repair, femoral block for total knee replacement or anterior cruciate ligament repair, intercostal nerve blocks for open chest surgery, or femoral and sciatic nerve blocks for leg amputation or foot and ankle surgery. For hip surgery, this could involve lumbar plexus block and lower volume sciatic block. This formulation could also be used for for nerve blocks (femoral and sciatic, lumbar plexus and sciatic) for hip or knee joint for joint replacement surgery.

For some of these medium volume uses, particularly with peripheral nerve blocks and plexus blocks, a high priority is to provide three features: anesthesia (near-complete insensitivity) for surgery for periods of 3-12 hours, analgesia (prolonged pain relief) after surgery for periods of at least 24 hours, while ensuring recovery from motor block to permit some strength in limb movement by a time frame of 24-48 hours For peripheral nerve blocks and plexus blocks with motor effects on arms and legs, based on the requirement for recovery from motor block from 24-48 hours, formulations with NeoSTX-bupivacaine without epinephrine are likely to be ideal, as detailed in the following tables.

TABLE 3

| Medium Volume Formulations (Adults) | | | |
|---|---|---|---|
| | Optimal | Preferred | Broader Range |
| Volumes | 25 ml | 20-40 ml | 15-50 ml |
| NeoSTX Concentrations | 0.4 mcg/ml | 0.3-0.5 mcg/ml | 0.2-2 Mcg/ml |
| Total NeoSTX Doses | 10 mcg | 8-20 mcg | 8-150 mcg |
| Bupivacaine Concentration | 0.2% (2 mg/ml) | 0.15-0.25% (1.5-2.5 mg/ml) | 0.1-0.3% (1-3 mg/ml) |
| Epinephrine Concentration | 0 mcg/ml | 0 mcg/ml | 1-5 mcg/ml |
| Typical clinical uses | Interscalene block for shoulder arm or hand surgery<br>Lumbar plexus block for hip replacement<br>Femoral or saphenous block for knee replacement or knee ligament reconstructions<br>Sciatic block for foot and ankle surgery<br>Femoral and sciatic blocks for leg amputations, foot or ankle surgery<br>Nerve blocks (femoral and sciatic, lumbar plexus and sciatic) for hip or knee joint for joint replacement surgery. | | |

TABLE 4

| Medium Volume Formulations (Children) (All listings of "/kg" refer to scaling by the child's body weight) | | | |
|---|---|---|---|
| | Optimal | Preferred | Broader Range |
| Volumes | 0.4 ml/kg | 0.3-0.5 ml/kg | 0.2-0.6 ml/kg |
| NeoSTX Concentrations | 0.4 mcg/ml | 0.3-0.5 mcg/ml | 0.2-2 Mcg/ml |
| Total NeoSTX Doses | 0.2 mcg/kg | 0.1-0.3 mcg/kg | 0.1-1.5 mcg/kg |
| Bupivacaine Concentration | 0.2% (2 mg/ml) | 0.15-0.25% (1.5-2.5 mg/ml) | 0.1-0.3% (1-3 mg/ml) |
| Epinephrine Concentration | 0 mcg/ml | 0 mcg/ml | 1-5 mcg/ml |
| Typical Clinical Uses | Interscalene block for shoulder surgery<br>Lumbar plexus block for congenital hip repairs<br>Femoral or saphenous block for knee ligament reconstructions<br>Sciatic block for foot and ankle surgery | | |

"Low Volume, Long Duration"

This formulation is for locations where very prolonged effect is designed, and where the volumes can be kept small to avoid spillover to other sites. An example is lumbar sympathetic blockade for complex regional pain syndrome/reflex sympathetic dystrophy or vascular insufficiency of the leg or for celiac plexus blockade for pancreatitis or cancer of the pancreas.

For lumbar sympathetic blockade, injection is performed to block a group of nerves that produce vasoconstriction in the leg. When these nerves are blocked, the result is increased blood flow to the leg, and reduced pain from certain diseases. For this nerve block, volume should be relatively low (preferred 8-20 mls) to avoid spillover to the somatic nerves of the lumbar plexus, which would make the leg weak. However, unlike medium volume, intermediate duration, it is desirable to have this type of block last as long as possible, since when performed using fluoroscopic guidance in small volumes, there is very little sensory or motor block. Therefore, relatively high concentrations of all three components should be used for this application to achieve durations of sympathetic blockade and increased local blood flow for at least four days.

A dosage formulation for low volume, long duration, includes as the active agents a combination of Bupivacaine in a concentration of 0.25%-0.5% (2.5-5 mg/ml), wherein 5-15 ml dosing gives a systemic bupivacaine dose in adults of no more than 75 mg, NeoSTX in a concentration range from 0.5-5 mcg/ml, wherein 5-15 ml dosing gives a systemic dose in adults of 5-75 mcg, and Epinephrine in a concentration range from 2.5-10 mcg/ml (1:500,000-1:100,000). An example is lumbar sympathetic blockade for complex regional pain syndrome/reflex sympathetic dystrophy or vascular insufficiency of the leg or for celiac plexus blockade for pancreatitis or cancer of the pancreas.

It is desirable to have this type of block last as long as possible, since when performed using fluoroscopic guidance in small volumes, there is very little sensory or motor block. Therefore, relatively high concentrations of all three components should be used for this application to achieve durations of sympathetic blockade and increased local blood flow for at least 3-4 days, and possibly longer. Other applications that can involve this low volume, long duration use would include sciatic nerve blockade of prolonged duration where rapid motor recovery is not an issue, as for a lower leg amputation.

TABLE 5

| Low Volume Formulations (Adults) | | | |
|---|---|---|---|
| | Optimal | Preferred | Broader Range |
| Volumes | 15 ml | 8-20 ml | 5-25 ml |
| NeoSTX Concentrations | 1 mcg/ml | 0.6-1.5 mcg/ml | 0.4-5 Mcg/ml |
| Total NeoSTX Doses | 15 mcg | 10-30 mcg | 5-80 mcg |
| Bupivacaine Concentration | 0.2% (2 mg/ml) | 0.2-0.4% (2-4 mg/ml) | 0.1-0.5% (1-5 mg/ml) |
| Epinephrine Concentration | 5 mcg/ml | 2.5-7.5 mcsg/ml | 1-5 mcg/ml |
| Typical clinical uses | Lumbar sympathetic nerve block for reflex sympathetic dystrophy or peripheral vascular disease<br>Celiac plexus block for chronic pancreatitis or pancreatic cancer<br>Sciatic nerve blockade of prolonged duration where rapid motor recovery is not an issue, as for a lower leg amputation | | |

TABLE 6

| Low Volume Formulations (Children) | | | |
|---|---|---|---|
| | Optimal | Preferred | Broader Range |
| Volumes | 0.25 ml/kg | 0.15-0.4 ml/kg | 0.1-0.5 ml/kg |
| NeoSTX Concentrations | 1 mcg/ml | 0.6-1.5 mcg/ml | 0.4-5 Mcg/ml |
| Total NeoSTX Doses | 0.25 mcg/kg | 0.1-0.5 mcg/kg | 0.05-1.2 mcg/kg |
| Bupivacaine Concentration | 0.2% (2 mg/ml) | 0.2-0.4% (2-4 mg/ml) | 0.1-0.5% (1-5 mg/ml) |
| Epinephrine Concentration | 5 mcg/ml | 2.5-7.5 mcsg/ml | 1-5 mcg/ml |
| Typical clinical uses | Lumbar sympathetic nerve block for reflex sympathetic dystrophy in adolescents<br>Sciatic nerve block for lower leg amputation for congenital malformations or cancer | | |

Two Drug Combinations of NeoSTX+BPV

A non-sustained release agent that reliably gives 6-12 hours of surgical-grade nerve block followed by up to approximately 48 h of lesser blockade without additional treatment is desirable. The former period would be useful intra-operatively as well as in the immediate post-op period; the latter would provide decreasing analgesia and allow increasing use of the involved body part as healing progresses. NeoSTX+BPV can produce this duration of block.

The present invention will be further understood by reference to the following non-limiting examples.

Example 1: Neosaxitoxin (NeoSTX) with Bupivacaine Provides Long-Duration Local Analgesia in Clinical Trials without an Increase in Toxicity A recent study of NeoSTX in sheep using subcutaneous injection showed that bupivacaine did not worsen surrogate measures of respiratory or neuromuscular toxicity from NeoSTX. In a separate model, deliberate intravenous infusion of NeoSTX showed remarkably slight cardiovascular toxicity, far less than in comparable previous studies of bupivacaine. The current study further investigates the dose response of NeoSTX and NeoSTX-bupivacaine combinations on neurobehavioral measures of rat sciatic nerve blockade, as well as on local and systemic toxicities of these combinations. These experiments were performed as preclinical studies for an Investigational New Drug Application, using NeoSTX formulations manufactured for clinical use in a planned phase 1 clinical trial.

The hypotheses were the following: 1) at fixed NeoSTX doses, addition of bupivacaine increases the intensity and duration of rat sciatic nerve blockade; 2) in the presence or absence of bupivacaine, intensity and duration of block increases with NeoSTX dose; 3) the histologic effects of NeoSTX (in saline or in combination with bupivacaine) on rat sciatic nerve are benign over the intended dose range, and not statistically different from those of vehicle or untreated nerves; 4) in a model of rapid accidental intravenous infusion, NeoSTX and bupivacaine separately generated respiratory and electrocardiographic endpoints with distinct time courses. Combinations using full concentrations of both NeoSTX and bupivacaine developed systemic toxicity more rapidly (i.e. with shorter infusion time and lower cumulative dose), while half-concentration combinations of each component developed toxicity more slowly, i.e. with a greater cumulative dose.

Materials and Methods

Methods:

NeoSTX, 0.25% bupivacaine, or combination was given by sciatic nerve injection to Sprague-Dawley rats. Sensory-nocifensive function was assessed by hotplate and Von Frey filament testing. Motor-proprioceptive function was assessed by extensor postural thrust. Seven days later, sciatic nerves were dissected, and histologically examined for toxicity. LD50 was also calculated for NeoSTX and NeoSTX-bupivacaine combination after sciatic injection. To model accidental intravenous overdose, isoflurane anesthetized, spontaneously breathing rats received infusions of either NeoSTX alone, bupivacaine alone, or NeoSTX-bupivacaine combinations until they reached respiratory and electrocardiographic endpoints.

Drugs

In the sciatic nerve injection model, drugs were prepared on the day of the experiment and injectate volume was fixed at 0.3 mL. NeoSTX (*Proteus* SA, Chile) was transported and stored according to Children's Hospital Boston safety standards, in compliance with the Harvard Committee on Microbiological Safety. NeoSTX stock contains 20 mcg/mL of neosaxitoxin at pH 4.5.

NeoSTX was diluted in 0.9% saline or bupivacaine hydrochloride (SENSORCAINE®, APP Pharmaceuticals, Schaumberg, Ill.). Depending on the intended final NeoSTX concentration, commercial vials of bupivacaine as either bupivacaine 5 mg/ml (0.5% or bupivacaine 2.5 mg/ml (0.25%) were used to reach final bupivacaine concentrations of 2 mg/ml (0.2%) in the final injectates. In the IV overdose model infusion concentrations were as follows: bupivacaine 2 mg/ml, NeoSTX 1.88 mcg/ml, full concentration combination bupivacaine 2 mg/ml and NeoSTX 1.88 mcg/ml, half-concentration combination: bupivacaine 1 mg/ml and NeoSTX 0.94 mcg/ml. Infusion rates were adjusted according to animal weight to ensure delivery of constant weight-scaled drug delivery rates. Thus, as single drugs, bupivacaine was administered at 3.2 mg/kg/min and NeoSTX as 3 mcg/kg/min. Full-dose combination animals received both bupivacaine 3.2 mg/kg/min and NeoSTX as 3 mcg/kg/min, while half-dose combination animals received bupivacaine at 1.6 mg/kg/min and NeoSTX 1.5 mcg/kg/min), and all animals received a constant weight-scaled fluid administration rate of 1.6 ml/kg/min.

Animal Care

Male Sprague-Dawley rats were obtained from Charles River Laboratories (Wilmington, Mass.): Young adults weighing 200 to 250 g were employed for the sciatic injection model and 325-400 g animals for the IV overdose model. Animals were cared for and sacrificed in compliance with protocols approved by the Institutional Animal Care and Use Committee at Children's Hospital. Handling procedures were developed to habituate animals to the testing paradigm and minimize stress-induced analgesia.

Sciatic Injection

Rats were briefly anesthetized with isoflurane by nose cone. A needle was introduced posteromedial to the greater trochanter, pointing in anteromedial direction. Once bone was contacted, 0.3 mL of solution was injected. The left leg was always used for blocks; the right served as a control and measure of systemic toxicity (Kohane, et al., *Anesthesiology,* 1998:119-131).

Neurobehavioral Testing

A neurobehavioral assessment battery modified from Thalhammer et al. that employs measures of sensory-nocifensive and motor-proprioceptive impairments to assess duration and intensity of blockade following sciatic perineural injection (Thalhammer, et al., *Anesthesiology,* 1995; 82:1013-1025) was used. Investigators were blinded to dose and treatment assignment. Sensation was first assessed using Von Frey filament (VF) testing (Touch-Test Sensory Evaluator, North Coast Medical Inc., CA). After brief habituation to a wire mesh cage, Von Frey hairs of ascending force were applied until observation of paw withdrawal. Care was taken to apply filaments only on lateral plantar surfaces receiving reliable innervation by the sciatic nerve. Filaments were applied in an escalating series until withdrawal was observed or until the maximum of 300 g was reached (Yahalom, et al., *Anesthesiology,* 2011; 114(6):1325-1335). Strength of Extensor Postural Thrust (EPT) in grams exerted on a balance and time to withdrawal from hotplate set at 56 degrees Celsius were measured as described in Kohane, et al. (Kohane 2000)

Neurobehavioral measures were taken at pre-injection baseline, 15 minutes, 1, 2, 3, 4, 6, 8, 10, and 12 h on the $1^{st}$ day and then every 4 h on the second day until motor recovery. At each time point, three measurements of EPT force and hotplate latency were taken and averaged. Previous studies of site 1 sodium blockers using this paradigm have shown that higher doses cause transient contralateral impairments of neurobehavioral measures, reflecting systemic analgesia and/or systemic weakness (Kohane, et al., *Reg. Anesth. Pain Med.,* 2001; 26(3)239-45).

In previous studies, injections with 0.3 ml of bupivacaine 2.5 mg/ml resulted in complete block (based on cutoffs defined later in this paragraph) for >98% of animals. In analyses, the assumption that incomplete block with test formulations reflects true pharmacologic effects of that dose, rather than a technical injection failure, was made. Previous work employed cutoffs to qualify animals as achieving a sensory or motor block: 7 s for thermal latency, 40 g for extensor postural thrust. 50% recovery was defined as 7 s and if cutoff were not reached then block duration was considered zero. It was found the use of these cutoffs may discount degrees of sensory and motor impairment of potential clinical significance. To improve upon these cut-offs, the greatest change from baseline to 15 minutes after vehicle injection was calculated and these values used as the threshold for a hotplate and EPT block (0.8 s and 8 g, respectively). Block threshold was considered to be 60 g for Von Frey testing. Recovery was defined as return to the same values.

Histological Procedures

Seven days after sciatic injection, rats were given an overdose of pentobarbital (150 mg/kg) and fixed by transcardiac perfusion in two stages: 100 mL of 0.9% saline was infused, followed by 200 mL of a modified-Karnovsky fixative containing 2.5% glutaraldehyde and 1.25% paraformaldehyde in 0.1M phosphate buffer. The left and right sciatic nerves were dissected and stored in dilute fixative at 4° C. Sciatic tissue was plastic embedded using standard osmium tetroxide electron microscopy protocol, cut to semi-thin sections and stained with toluidine blue. Sections were analyzed by an experienced neuroscientist (G.C.), using the scoring system of Estebe & Myers; this neuroscientist remained blinded to group assignments throughout (Estebe, *Anesthesiology,* 2004; 100:1519-25).

Systemic Toxicity with Sciatic Perineural Injection.

Sublethal systemic toxicity was assessed by measurement of right hindlimb sensory-nocifensive and motor-proprioceptive impairments following left hindlimb sciatic injections as described in the "Neurobehavioral Testing" paragraphs above. At higher doses of NeoSTX, alone or in combination with bupivacaine, increasing numbers of animals developed apnea or gasping respiration. To minimize distress in this paradigm involving awake animals, any animal developing apnea or gasping was immediately euthanized with intraperitoneal pentobarbital (100 mg/kg), and this was taken as a lethal event. LD50 calculation is described in the Statistical Procedures section below.

Systemic Toxicity with Intravenous Infusion

To model an accidental IV injection, isoflurane-anesthetized, spontaneously breathing rats received infusions via tail vein cannula of drug-containing solution until the endpoint of asystole. 26 rats were randomly assigned to 4 groups: NeoSTX plain (n=6); bupivacaine (n=7); full concentration NeoSTX-bupivacaine combination (n=7); and half concentration NeoSTX-bupivacaine combination (n=6), using the drug concentrations and infusion rates detailed in the section entitled "Drugs" above. Anesthesia was induced by inhalation of isoflurane 3-5% in oxygen and maintained by isoflurane 1% via nose cone. A catheter was placed in the tail vein, flushed with 2 mL of 0.9% saline and connected to a Medfusion syringe pump (Smiths Medical, St Paul, Minn.). Vital signs were monitored and physiologic data acquired continuously using Powerlab equipment and LabChart software (AD Instruments, Sydney, Australia). Baseline measurements are taken (subsequent offline analysis) once all monitoring equipment is calibrated and connected (ECG, temperature, pulse oximeter, Bain circuit pressure transducer, and tail vein plethysmograph), tail vein accessed, and the rat was maintained in a stable plane of anesthesia at 1% inspired isoflurane in oxygen for at least 5 minutes. Infusions as described in the paragraph entitled "Drugs" above were initiated immediately following a short period of baseline recording and continued until asystole was reached. Primary endpoints for analysis were as follows: (1) apnea (undetectable pressure changes in the Bain circuit), and (2) asystole. Secondary endpoints were: bradycardia (heart rate <270), deleterious change in electrocardiographic waveform (including either heart block, wide QRS complex, ectopic atrial or ventricular beats, or prolonged QTc interval), and loss of caudal artery pulsatility by plethysmography.

Statistical Procedures

All measurements are summarized as medians with interquartile ranges or mean±standard deviation of the mean. Changes in neurobehavioral function tests were assessed in a nonparametric Friedman model with treatment and NeoSTX dose as fixed factors with Bonferroni-adjusted P values in multiple comparisons (Montgomery, D., Design and Analysis of Experiments, $5^{th}$ Ed. 2001, New York, N.Y.: John Wiley & Sons, Inc.). Combinations of clinically relevant doses of 1 or 2 mcg/kg were explored further with Mann-Whitney U-tests. Nerve histology was analyzed with a Kruskal-Wallis model. Probit analysis using maximum likelihood was applied to calculate the median lethal dose ($LD_{50}$) for each drug treatment with likelihood ratio 95% confidence intervals obtained by the profile log-likelihood method In the IV overdose model, time to event data were summarized using Kaplan-Meier curves. Multiple pairwise comparisons of survival curves to Bupivacaine alone were conducted and P values less than 0.017 were considered statistically significant (Finney, *Arch. Toxicol.,* 1985; 56:215-218; Faraggi, et al., *Statist. Med.,* 2003; 22:1977-1988). Statistical analysis was performed using the SPSS statistical package (version 19.0, SPSS Inc./IBM, Chicago, Ill.).

Results:

Over a range of doses, addition of bupivacaine to NeoSTX caused more intense and more prolonged block of nocifensive and motor-propriceptive function compared to NeoSTX alone. See Table 7. Histologic injury scores overall were very low for all groups, with median and IQR values of 0 on an Estebe-Myers scale. With subcutaneous injection, addition of bupivacaine to NeoSTX produced no increase in systemic toxicity (LD50) compared to NeoSTX alone. With intravenous infusion, NeoSTX, bupivacaine, and combinations showed different time courses in reaching respiratory versus electrocardiographic endpoints. See Table 8.

Neurobehavioral Measures

Block Intensity

FIGS. 1A-1F show the dependence of block intensity at 15 minutes on the dose of NeoSTX administered in the presence or absence of bupivacaine. All bupivacaine-containing formulations were associated with complete blockade of all three behavioral measures at that time point. In the absence of bupivacaine, doses of NeoSTX alone less than or equal to 3 mcg/kg produced incomplete block for a majority of animals.

Duration of Block

Figure 2A:
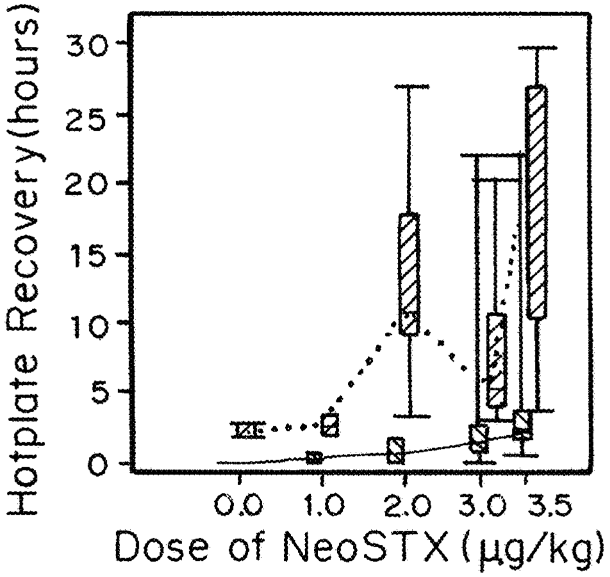
FIGS. 2A-2F show the duration of rat sciatic block for NeoSTX in saline and NeoSTX-Bupivacaine.
Figure 2B:
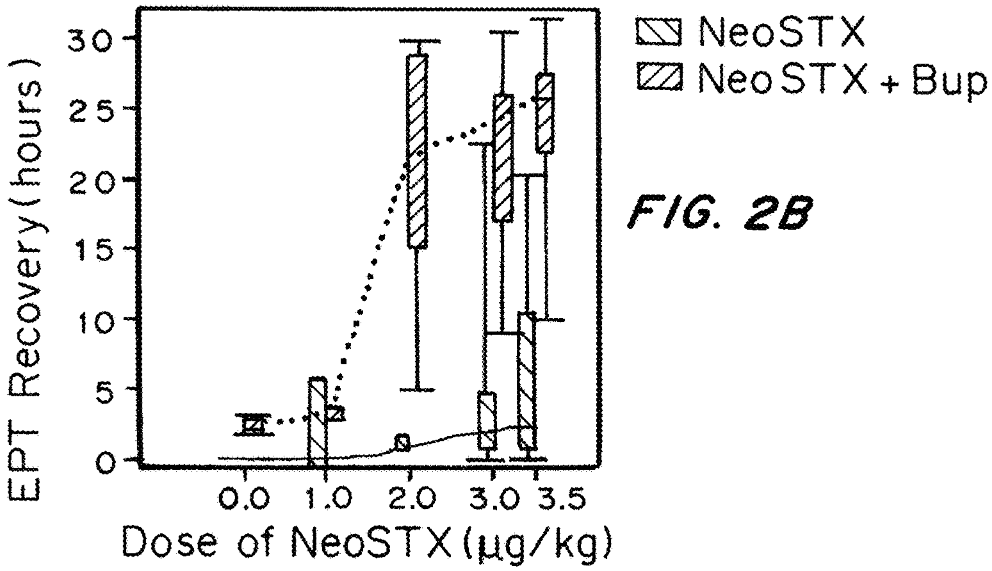

In comparison to animals receiving injections of NeoSTX in saline, addition of bupivacaine produced substantial increases in time to 100% recovery from thermal and mechanical sensory-nocifensive and motor-proprioceptive blockade (P<0.001). Results are shown in FIGS. 2A-2F. Bonferroni-corrected pairwise analysis of groups receiving increasing doses of NeoSTX with and without bupivacaine, demonstrated that bupivacaine group had significantly longer block durations at all doses greater than 1 mcg/kg (FIG. 2A).

Median time to 100% recovery after injection of 0.25% bupivacaine alone was 2.2 h (1.9-2.9) for hotplate testing, 2.2 h (1.8-2.6) for EPT testing, and 1.9 h (1.7-2.7) for VF testing. Injection of 0.25% bupivacaine combined with 1 mcg/kg of NeoSTX yielded significantly increased time to 100% recovery in Von Frey (2.8 h, 2.2-3.5, P=0.05) and EPT tests (3.1 h, 2.8-3.9, P<0.001), but did not increase time to 100% recovery of hotplate nocifensive behavior (2.5 h, 2.0-3.5, P=0.4). Time to 50% recovery, in hours, was calculated for all tests and doses and is displayed in Table 7. Time to 50% Von Frey recovery was significantly increased in animals after 1 mcg/kg NeoSTX and bupivacaine compared to bupivacaine alone (2.5 h, 1.7-2.9 compared to 1.5 h, 1.5-2.1, P=0.03) whereas EPT and hotplate were not significantly different. However, combining 2 mcg/kg of NeoSTX with bupivacaine caused a significant and substantially larger increase in time to 100% recovery of hotplate response (10.8 h, 9.1-17.8, P<0.001), EPT response (22 h, 15-28, P<0.001), and Von Frey response (4.7 h, 3-11, P<0.001).

TABLE 7

Time to 50% recovery of injected limb by hotplate, EPT, and Von Frey testing.

| Treatment Group | Neurobehavioral Test Hotplate | Extensor Postural Thrust | Von Frey |
|---|---|---|---|
| Bupivacaine (n = 20) | 1.5 (1.49-2.13) | 2.01 (1.51-2.39) | 1.55 (1.51-2.09) |
| 1 mcg NeoSTX (n = 4) | 0.00 (0.00-0.00) | 0.00 (0.00-1.50) | 0.00 (0.00-1.31) |
| 1 mcg NeoSTX + Bup (n = 8) | 1.61 (1.52-2.72) | 1.73 (0.78-1.92) | 2.52 (1.66-2.92) |
| 2 mcg NeoSTX alone (n = 8) | 0.00 (0.00-1.03) | 0.00 (0.00-1.57) | 0.00 (0.00-1.14) |
| 2 mcg NeoSTX + Bup (n = 11) | 3.77 (2.61-10.13) | 9.09 (3.84-17.77) | 3.63 (2.53-8.50) |
| 3 mcg NeoSTX alone (n = 20) | 0.16 (0.00-1.48) | 0.00 (0.00-0.56) | 0.00 (0.00-1.31) |
| 3 mcg NeoSTX + Bup (n = 27) | 3.53 (2.78-4.63) | 17.91 (12.06-22.51) | 4.52 (3.51-9.00) |
| 3.5 mcg NeoSTX alone (n = 12) | 0.92 (0.00-2.01) | 0.00 (0.00-7.42) | 0.00 (0.00-1.87) |
| 3.5 mcg NeoSTX + Bup (n = 13) | 10.32 (3.66-11.56) | 20.58 (18.12-24.04) | 6.11 (3.28-11.94) |

Values are median (IQR).

Systemic Toxicity

Figure 2C:
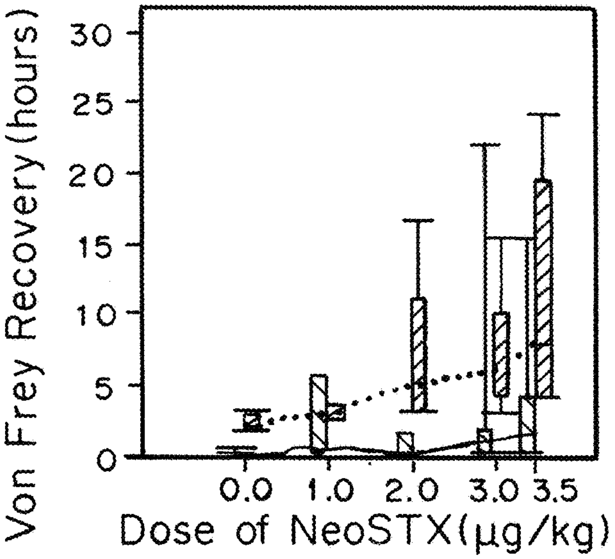
Figure 2D:
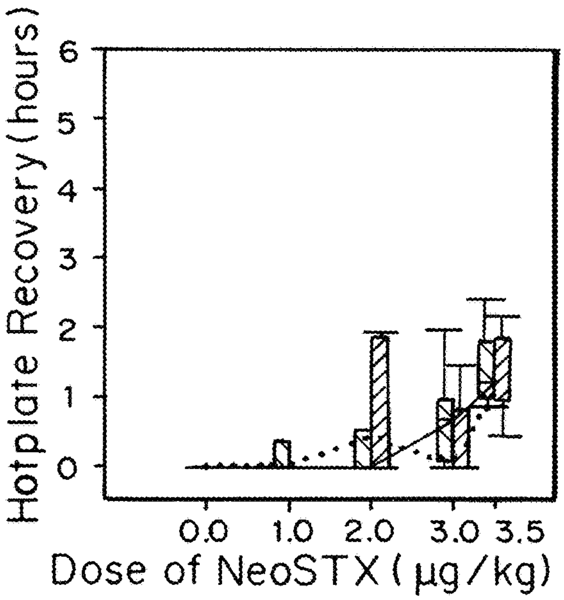
Figure 2E:
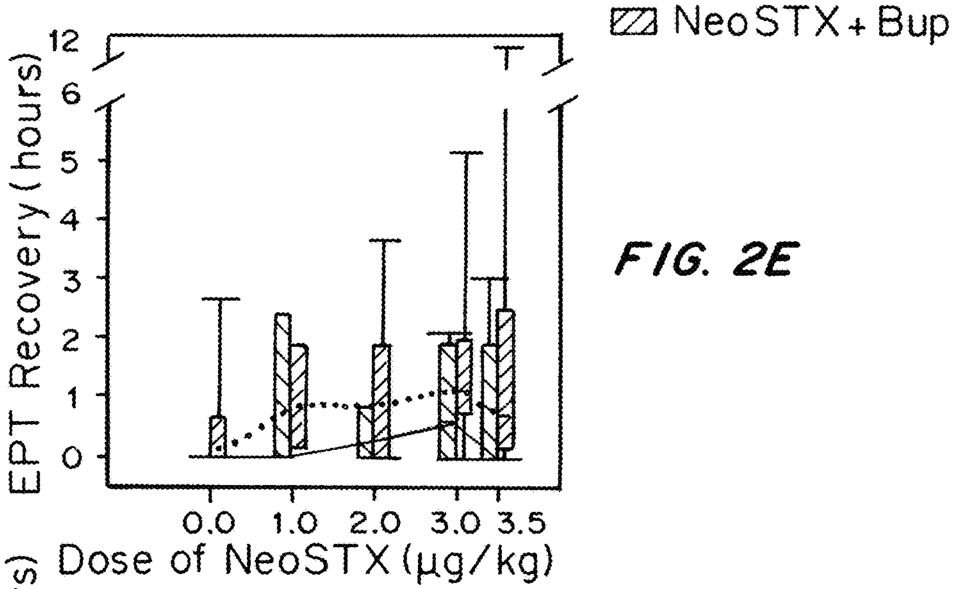
Figure 2F:
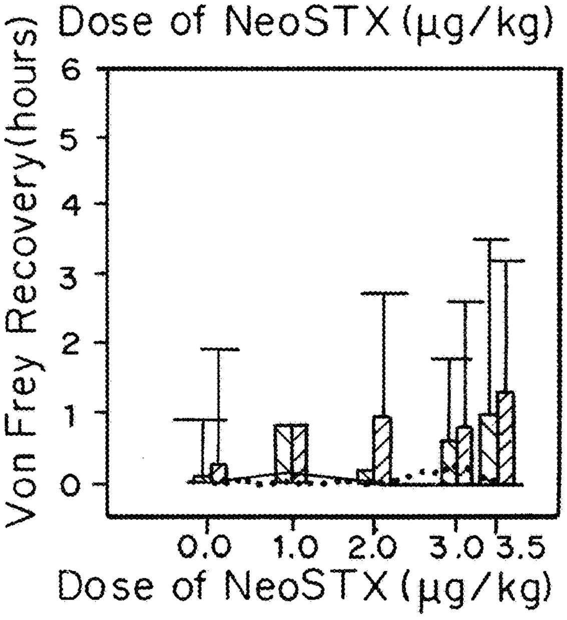
Figure 3:
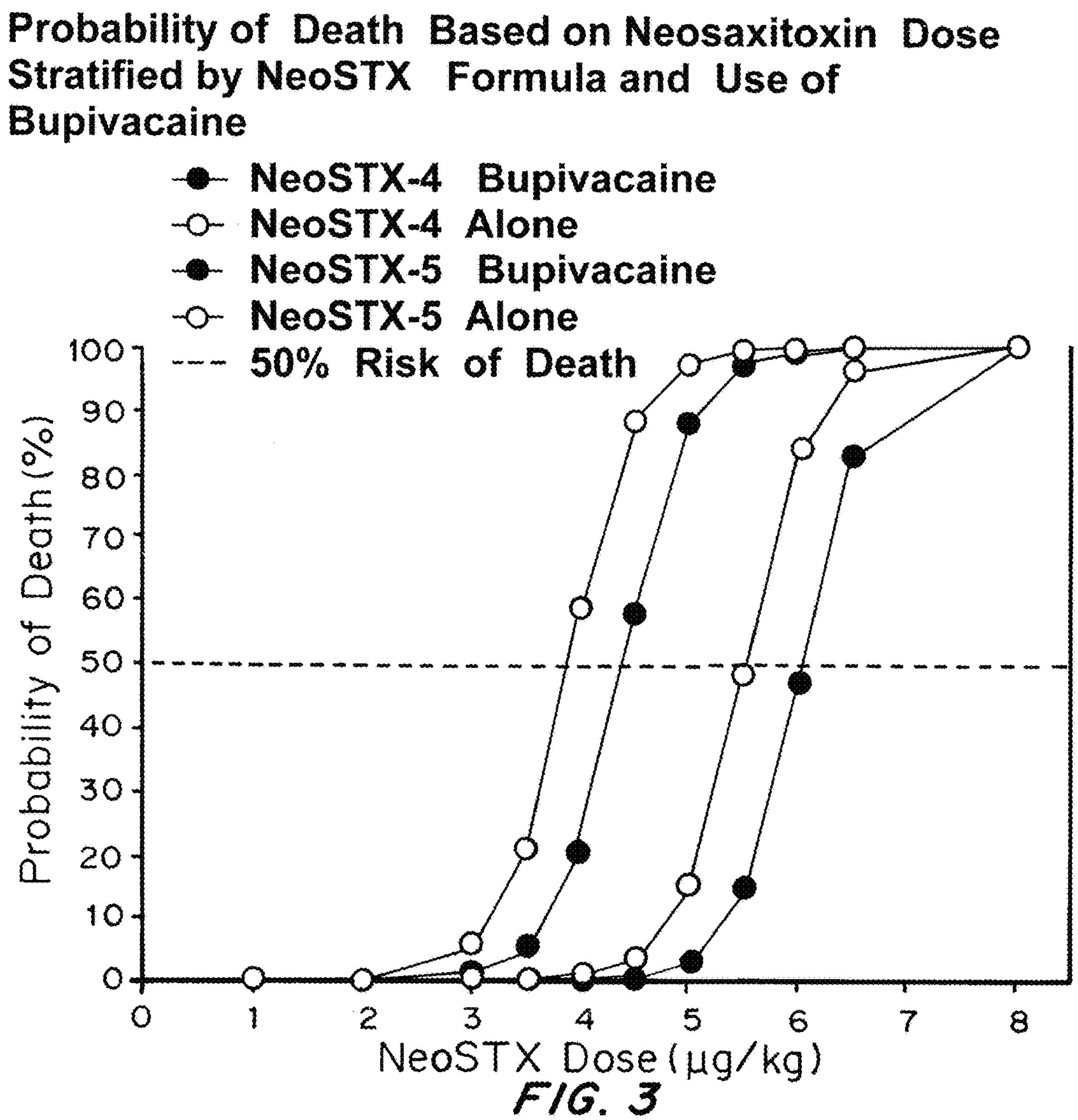
FIG. 3 shows that addition of Bupivacaine reduces the systemic toxicity of NeoSTX (raises the LD50). NeoSTX 4 and NeoSTX 5 refer to two different formulations prepared in different manufacturing facilities over a year apart.

As a marker for systemic drug distribution after sciatic injection, neurobehavioral measures were obtained from the uninjected right limb. Compared to bupivacaine alone, injection of NeoSTX with bupivacaine was associated with increased intensity EPT block at 15 minutes (P=0.001), but was not significantly associated with changes in hotplate or Von Frey response (FIGS. 2C, 2E). In the Bonferroni-corrected model using NeoSTX dose and presence of bupivacaine as variables, combination of NeoSTX with bupivacaine produced hotplate (2A, 2D) and EPT (2B, 2E) blockade significantly greater than bupivacaine alone in the contralateral limb at doses of 3 mcg/kg (P=0.011 and P=0.038, respectively) and 3.5 mcg/kg (P<0.001 and P=0.036, respectively). For the relatively small contralateral blocks observed, ANOVA revealed no significant differences in time to 100% recovery in the contralateral limb between NeoSTX and NeoSTX-bupivacaine combination animals when NeoSTX dose was less than 3 mcg/kg (FIG. 2E).

LD50 Testing

Given the absence of mortality in the 3 mcg/kg NeoSTX group, the dosage was escalated to a maximum of 8 mcg/kg. This maximum dose yielded 100% mortality within 30 minutes of administration, for both NeoSTX alone and in combination with bupivacaine. In all animals, death was due to terminal apnea. $LD_{50}$ was calculated at 4.9 mcg/kg (95% CI=4.2-6.2) for NeoSTX alone and 5.7 mcg/kg (95% CI=4.9-7.9) for NeoSTX with bupivacaine (FIG. 4). Escalating NeoSTX across the range measured was significantly associated with increased lethality (Z=5.82, P<0.001) and the effect of decreased mortality by adding bupivacaine approached significance (Z=1.86, P=0.06). The point of emphasis here is that co-administration of bupivacaine decreased, rather than increased, the systemic toxicity of NeoSTX.

TABLE 8

Vital signs at baseline for intravenous overdose model among 4 Treatment Groups (n = 26).

| Characteristic | Treatment Groups Bupivacaine (n = 7) | NeoSTX (n = 6) | High Dose Combination (n = 7) | Low Dose Combination (n = 6) | P |
|---|---|---|---|---|---|
| Weight (kg) | 0.34 ± 0.03 | 0.35 ± 0.02 | 0.36 ± 0.02 | 0.34 ± 0.03 | 0.19 |
| Temperature (C. °) | 37.7 ± 0.3 | 37.6 ± 0.4 | 37.4 ± 0.4 | 37.4 ± 0.5 | 0.59 |
| Heart Rate (BPM) | 354 ± 33 | 377 ± 35 | 359 ± 32 | 357 ± 26 | 0.58 |
| Respiratory Rate (BPM) | 71 ± 12 | 82 ± 11 | 77 ± 12 | 78 ± 11 | 0.41 |
| QT Interval (ms) | 0.10 ± 0.04 | 0.11 ± 0.03 | 0.12 ± 0.02 | 0.14 ± 0.03 | 0.19 |
| PR Interval (ms) | 0.04 ± 0.01 | 0.05 ± 0.01 | 0.06 ± 0.02 | 0.05 ± 0.01 | 0.09 |
| QRS Interval (ms) | 0.015 ± 0.003 | 0.013 ± 0.003 | 0.014 ± 0.003 | 0.015 ± 0.003 | 0.61 |

NeoSTX = Neosaxitoxin.
Mean ± SD,
P values based on ANOVA.

Nerve Histology

Estebe-Myers scoring of nerve injury revealed a very benign histologic profile after sciatic injection. For all treatment conditions, the median Estebe-Myers nerve injury score was 0 (IQR 0-0). No nerve was rated at a score of 3 or 4. There were no statistical differences between any treatment group and non-injected control (right) sciatic nerves. Total numbers of nerves examined included the following: vehicle 19, bupivacaine 0.25% plain 19, contralateral (non-injected right side) 16, NeoSTX 1 mcg/kg in saline 4, NeoSTX 1 mcg/kg in bupivacaine 8, NeoSTX 2 mcg/kg in saline 4, NeoSTX 2 mcg/kg in bupivacaine 7, NeoSTX 3 mcg/kg in saline 19, NeoSTX 3 mcg/kg in bupivacaine 27, NeoSTX 3.5 mcg/kg in saline 12, NeoSTX 3.5 mcg/kg in bupivacaine 13, NeoSTX 4 mcg/kg in saline 1, NeoSTX 4 mcg/kg in bupivacaine 6. As a validation check on the blinded histologist's readings, slides were obtained from sections of positive control nerves taken from animals who had received deliberate nerve injury (loose ligation model), processed under the same protocol. These positive control nerves all received high injury ratings, with Estebe-Myers scores of 3 or 4.

This demonstrates that combining NeoSTX with bupivacaine increases duration and reliability of sciatic block without increasing neurotoxicity or increasing systemic toxicity (reducing $LD_{50}$) after subcutaneous injection.

The study demonstrates that, in rats, sciatic co-injection of 0.25% bupivacaine with NeoSTX increased intensity and duration of nocifensive blockade to thermal stimulus without increase in neurotoxicity or lethality. When bupivacaine is added to 3 mcg/kg NeoSTX, a weight-scaled dose approximately 2-fold greater than that employed previously in humans, the percentage of effectively blocked animals increased from 50 to 100%. In clinically relevant doses (1 and 2 mcg/kg) combining NeoSTX with bupivacaine led to a significant increase in intensity and duration of sensory-nocifensive block.

Figure 4A:
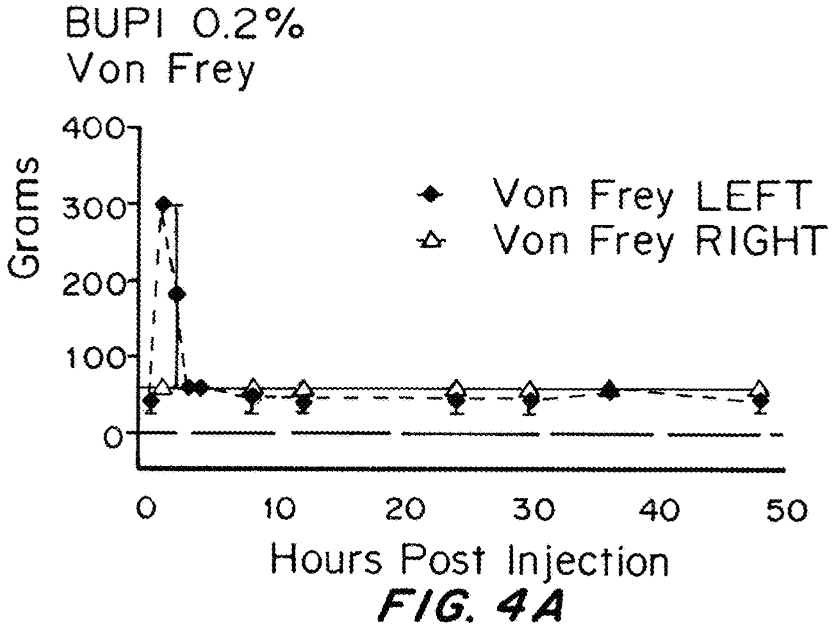
FIGS. 4A-4C show that block durations are longest with NeoSTX-Bupivacaine-Epinephrine, intermediate with NeoSTX-Bupivacaine, and shortest with bupivacaine alone.
Figure 4B:
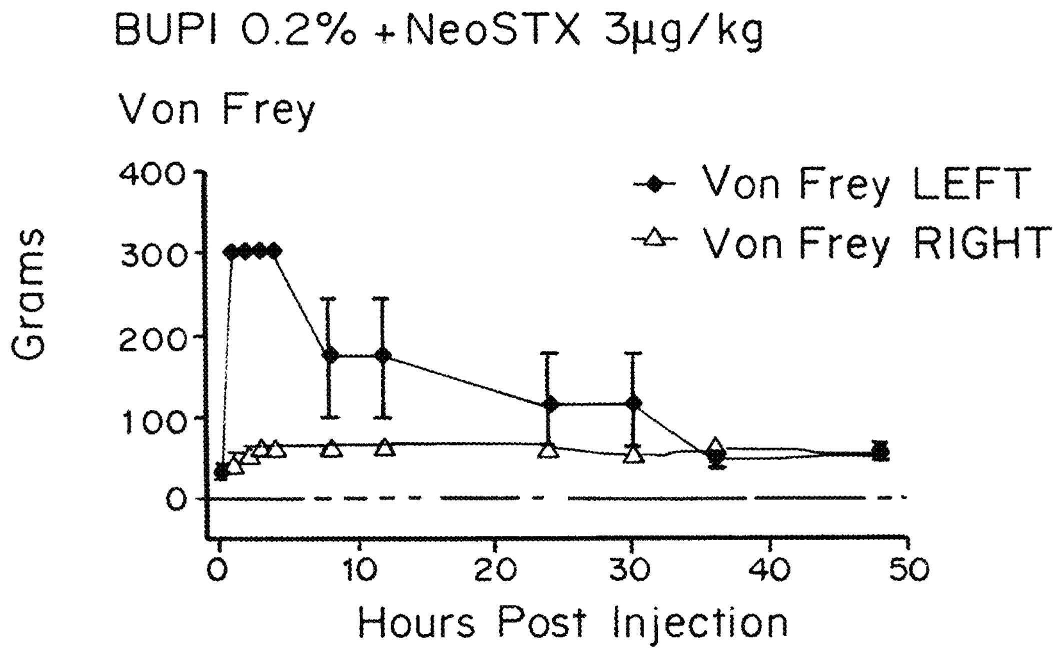
Figure 4C:
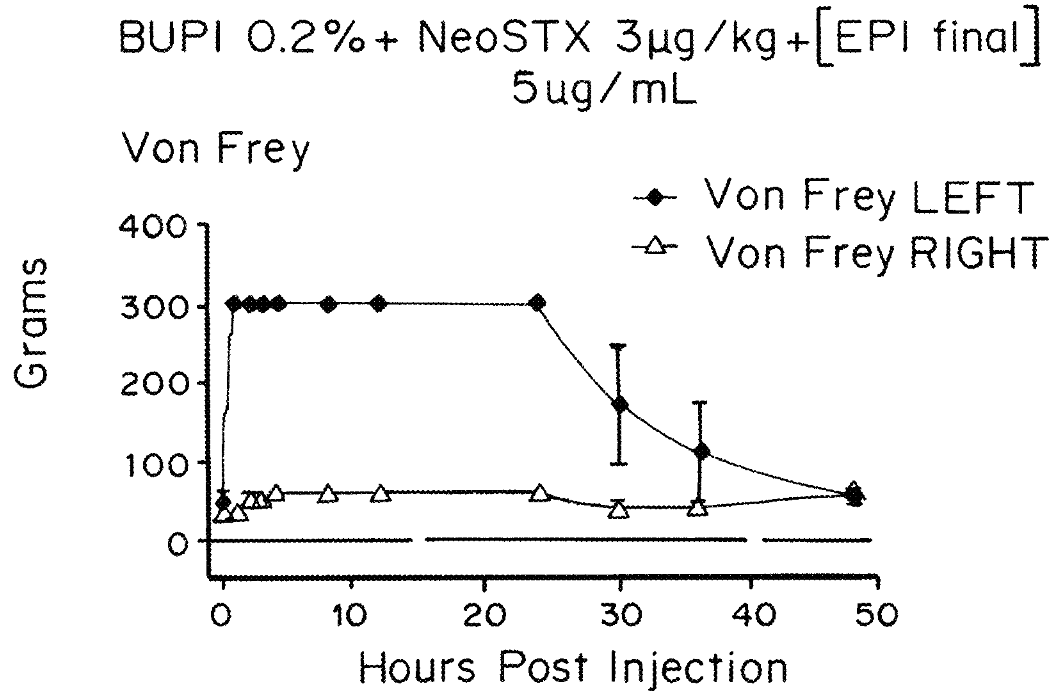

In FIGS. 4A-C, the intensity and duration of sensory blockade in groups of rats receiving either bupivacaine 0.2% plain (FIG. 4A), bupivacaine 0.2% with NeoSTX 3 mcg/kg (FIG. 4B), and bupivacaine 0.2% with NeoSTX 3 mcg/kg and epinephrine 5 mcg/ml (FIG. 4C). It is apparent that the three-way combination gives more intense and prolonged blockade compared to the two-way combination. This predicts that the three-way combination will provide more intense and prolonged pain relief than the two-way combination, which is particularly important in the "high-volume" and "medium volume" clinical settings described above.

A model for study of systemic toxicity was used. An intramuscular (sciatic perineural) injection model was used to simulate systemic toxicity in an extravascular site, as intended for nerve blockade or infiltration in clinical use. In this model, co-injection of bupivacaine along with NeoSTX slightly reduces systemic toxicity compared to animals receiving the same dose of NeoSTX in saline. In this model, the bupivacaine dose is below the range that produces cardiotoxicity. The presumed mode of death is from respiratory muscle weakness and some vasodilatation due to the NeoSTX, and bupivacaine may reduce systemic toxicity from NeoSTX by local vasoconstriction at the injection site, thereby slowing the systemic uptake of NeoSTX. This conjecture is based on the known local vasoconstrictive effects of bupivacaine and previous regional blood flow experiments in rats following sciatic perineural injection of another site-1 sodium channel blocker, tetrodotoxin.

Since co-injection of bupivacaine increases the potency and duration of nerve block from NeoSTX while slightly reducing its systemic toxicity, the NeoSTX-bupivacaine combination provides a significant improvement in therapeutic index compared to NeoSTX alone. A formulation of NeoSTX developed for clinical trials provides prolonged longer duration sciatic nerve blockade than bupivacaine in rats. Co-injection with bupivacaine improves the reliability and duration of blockade compared to NeoSTX alone.

Example 2: Phase I Clinical Study in Adult Humans

Investigators at the University of Chile, Santiago, and a small biotech company, Proteus S.A, developed a bioreactor process to produce clinical grade NeoSTX efficiently, with excellent purity, stability, sterility and non-pyrogenicity. A series of preclinical safety and toxicologic studies in mice, rats, and sheep were performed at CHB and Toxikon, Inc. With approval oversight of the regional IRB and the Chilean Instituto de Salud Publica (ISP), the primary regulatory agency for drug approval and oversight in Chile, Dr. Rodriguez-Navarro and colleagues have conducted two Phase 1 volunteer trials (Rodriguez-Navarro, et al., *Anesthesiology,* 106: 339-345, 2009; Rodriguez-Navarro, et al., *Neurotox. Res.,* 2009; 16: 408-15) and two Phase 2 trials of NeoSTX as a prolonged duration local anesthetic for patients undergoing laparoscopic cholecystectomy (Rodriguez-Navarro, et al., *Reg. Anesth. Pain Med.,* 2011, 36:103-109; Rodriguez-Navarro—abstract for presentation at ESRA meeting, September 2010).

In the Phase 1 volunteer trials, doses of 10 or 50 mcg produced skin numbness with excellent local and systemic safety. Combinations of NeoSTX with either bupivacaine or epinephrine dramatically intensifies and prolongs the duration of cutaneous numbness compared to NeoSTX alone, which in turn gave more prolonged cutaneous numbness than bupivacaine (Rodriguez-Navarro, et al., *Neurotox. Res.,* 2009; 16: 408-15). Addition of epinephrine reduces systemic toxicity, and produces a robust prolongation of sensory blockade.

In two Phase 2 trials double-blind superiority trials of patients undergoing laparoscopic cholecystectomy under general anesthesia, comparing 100 mcg NeoSTX to bupivacaine for infiltration of the port sites, NeoSTX gave more prolonged analgesia than bupivacaine, and patients self-reported global ratings indicated more rapid postoperative recovery. To date, 181 patients in Chile have received NeoSTX in clinical trials without any serious adverse events.

Recent human studies demonstrated potency, safety and prolonged analgesic effects of NeoSTX by using skin infiltration with either 10 mcg or 50 mcg in Phase 1 studies with awake volunteers, and by using wound layer infiltration with 100 mcg in Phase 2 studies with patients undergoing laparoscopy cholecystectomy under general endotracheal anesthesia.

In the awake volunteers, there were no reports of weakness and there were no signs of respiratory or hemodynamic abnormalities, but detailed surrogate measures of subclinical Systemic Effects were not performed.

In the patients in the laparoscopic cholecystectomy trials, with double blind comparison to bupivacaine, the injections were performed under general endotracheal anesthesia with controlled ventilation. Therefore, immediate effects on symptoms and respiratory muscle strength could not be assessed. However, all subjects showed excellent respiratory effort at the end of surgery and none of the patients had a delay in extubation (duration of surgery was approximately 1 hour), and no signs of weakness or hypoventilation were noted on prolonged observation in the Post Anesthesia Care Unit (PACU).

Nevertheless, even though these Phase 2 studies in surgical patients suggest good systemic safety for NeoSTX in 100 mcg doses in anesthetized, mechanically ventilated subjects, it was essential to perform additional Phase 1 studies dose escalation studies beginning with smaller doses and using more precise surrogate measures of subclinical systemic effects to select a safe dose (with a minimal adverse event threshold) in awake young adult male subjects.

Materials and Methods

The primary aim of this Phase 1 study was to evaluate the systemic safety of Neosaxitoxin (NeoSTX), given by subcutaneous injection in combination with the commonly used local anesthetic, bupivacaine, and epinephrine. Secondary aims of this Phase 1 study were to establish the dose-dependence of intensity and duration of cutaneous sensory blockade (numbness to thermal and mechanical stimuli) of NeoSTX in saline compared to NeoSTX in combination with bupivacaine and epinephrine, to establish the local safety and tolerability of NeoSTX, when given by subcutaneous injection, and to measure the pharmacokinetics of NeoSTX following subcutaneous injection. A Phase I study was performed under an Investigator-Initiated FDA IND to further establish the systemic and local safety and dose response for cutaneous sensory blockade of NeoSTX via sub-cutaneous infiltration in healthy young adult male human volunteer subjects.

As detailed below, tingling of the lips, tongue and fingers occurs at doses that appear physiologically very safe. This protocol amendment reflects an expectation that NeoSTX would be used two dose ranges in subsequent Phase 2 studies: one that produces minimal systemic symptoms in awake subjects and a second somewhat higher dose range that is intended for use in sedated or anesthetized subjects in an operating room setting. This amendment involves dosing cohorts of subjects in an operating room setting and permits subjects to receive low dose anxiolysis with midazolam if the tingling is perceived as intense or very bothersome. It is therefore important to define safety in a dose range where the drug would be used in an operating room setting. A sequential dose escalation design will be used with groups 9 subjects in each dose step. In double blind fashion, each subject received two injections simultaneously in a 3 cm×3 cm square area on skin of the posterior aspect of the lower leg (calf), one on each side, in a randomized block design. Each subject received one injection with bupivacaine 0.2% alone on one side. On the other side, they received one of 2 possible solutions: (1) saline placebo, or (2) NeoSTX in combination with bupivacaine and epinephrine. In each dose group, only one of the injections involves placebo.

Test subjects were young adult males. Subcutaneous infiltration was performed using a 25 gauge 1½ inch needle. The 10 ml volume was distributed so that 2 ml is administered subcutaneously on each of the sides of the 3×3 cm square, and 2 ml is given across the diagonal.

Individuals were given NeoSTX in a dose of 5, 10, 15, 20, 30 or 40 mcg, 0.2% bupivacaine and 5 mcg epinephrine/ml. Epinephrine was routinely added to local anesthetic injections for two reasons: (1) to slow systemic uptake and reduce systemic blood concentrations and thereby reduce risks of systemic toxicity, and (2) to prolong the duration of local anesthesia.

The use of a within-subject paired dosing design with bupivacaine on one side and either NeoSTX in saline or NeoSTX in bupivacaine on the other side permits within-subject comparison of the intensity and duration of cutaneous analgesia with escalating doses of NeoSTX, with or without a fixed concentration of bupivacaine 0.2%, compared to the currently used standard, bupivacaine 0.2%.

The primary outcome measure of this phase I study is absence or presence of, frequency, and grade of AEs as defined by 21 CFR 312.32 as a function of NeoSTX at each dose step, given with or without bupivacaine. These adverse events measure systemic effects of due to NeoSTX.

The design is intended to define a threshold for systemic effects while reducing the likelihood of Adverse Events and Serious Adverse Events.

An Adverse Event (AE) refers to any untoward medical occurrence associated with the use of Neosaxitoxin in humans, whether or not considered drug related, as described in 21 CFR 312.32. The intensity (grade) of each AE was assessed using the following scale:

Grade 1 (Mild): Experiences which are usually transient, requiring no special treatment, and do not interfere with the subject's daily activities.

Grade 2 (Moderate): Experiences which introduce some level of inconvenience or concern the subject, and may somewhat interfere with daily activities, but are usually ameliorated by simple therapeutic measures (may include drug therapy).

Grade 3 (Severe): Experiences which are unacceptable or intolerable, significantly interrupt the subject's usual daily activity, and require systemic drug therapy or other treatment.

Grade 4 (Life-threatening): Experiences which cause the subject to be in imminent danger of death.

Grade 5 (Death): Subject fatality

Results for NeoSTX in Combination with Bupivacaine and Epinephrine

A full evaluation of dose cohorts at the 5 mcg, 10 mcg, 15 mcg, 20 mcg and 30 mcg level were completed and the 40 mcg cohort (n=10, still enrolling) has almost been completed. At the 40 mcg dose, a high rate of systemic effects in awake subjects was observed. As before, these effects involve systemic symptoms (tingling and numbness, and now nausea), but no signs of impending physiologic risk. The presence of nausea and vomiting for a brief period of time (one hour) following the injection was also observed in 8/10 patients. To date the patients have rated this as mildly bothersome. There has been no impairment of oxygenation or ventilation, no impairment of inspiratory force or vital capacity (respiratory muscle strength) and no impairment of grip strength, no changes in cardiac rhythm, and no hypotension.

In future clinical use for infiltration, it is likely that higher injection volumes, e.g. 30 mls, will be used. In principle, to block a surgical field that is three times as large requires roughly three times the injected volume of local anesthetic, and therefore three times the local anesthetic dose, when given at a fixed concentration. Systemic safety varies with total dose, while local efficacy and duration varies with local drug concentrations. The study showed that NeoSTX 30 mcg is a safe dose in these volunteers.

At a total dose of 10 mcg in the 10 ml injectate, the local NeoSTX concentration equals the expected concentration when used for wound infiltration in a volume of 30 mls.

High dose NeoSTX (30 mcg) group gives the maximum total dose for the proposed 30 ml vials for future infiltration analgesia.

Figure 5A:
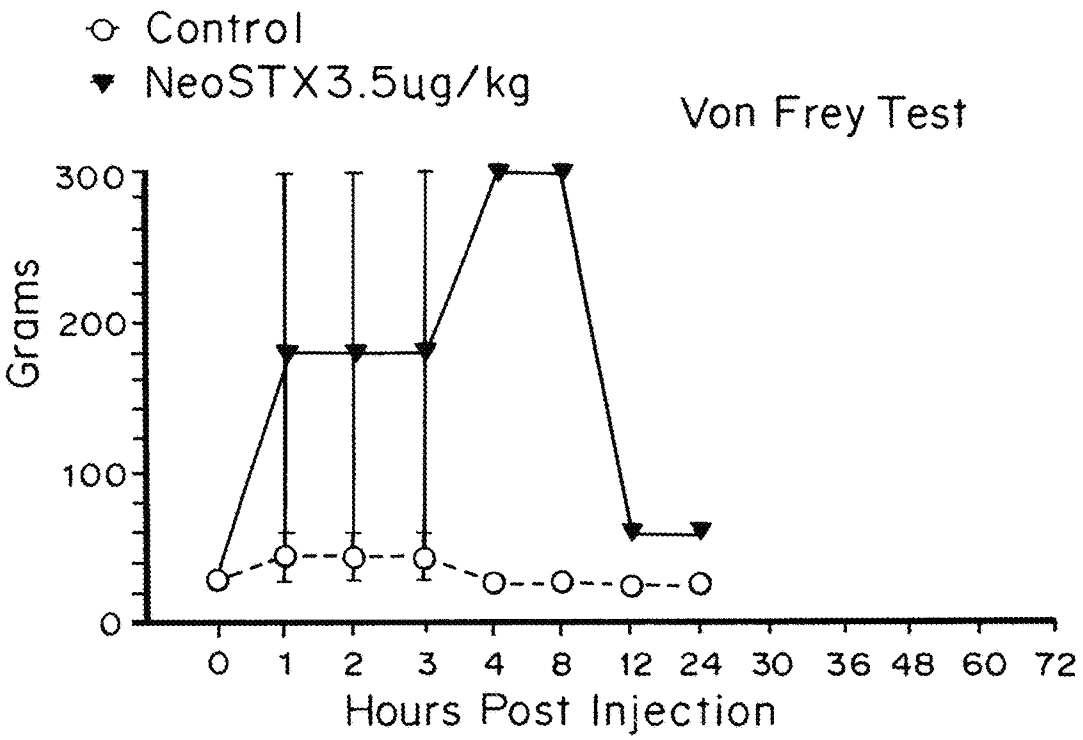
FIGS. 5A and 5B show that addition of Bupivacaine to NeoSTX improves block reliability and duration compared to NeoSTX-Saline, measured by rat sciatic nerve blockade. Addition of Epinephrine to NeoSTX-Bupivacaine produces further prolongation of block. The results demonstrate NeoSTX in saline produces inconsistent and delayed onset of mechanical sensory block and block is fully recovered by 12 hours, even at a slightly higher NeoSTX dose (3.5 mcg/kg) than was used in FIG. 5B (3 mcg/kg).
Figure 5B:
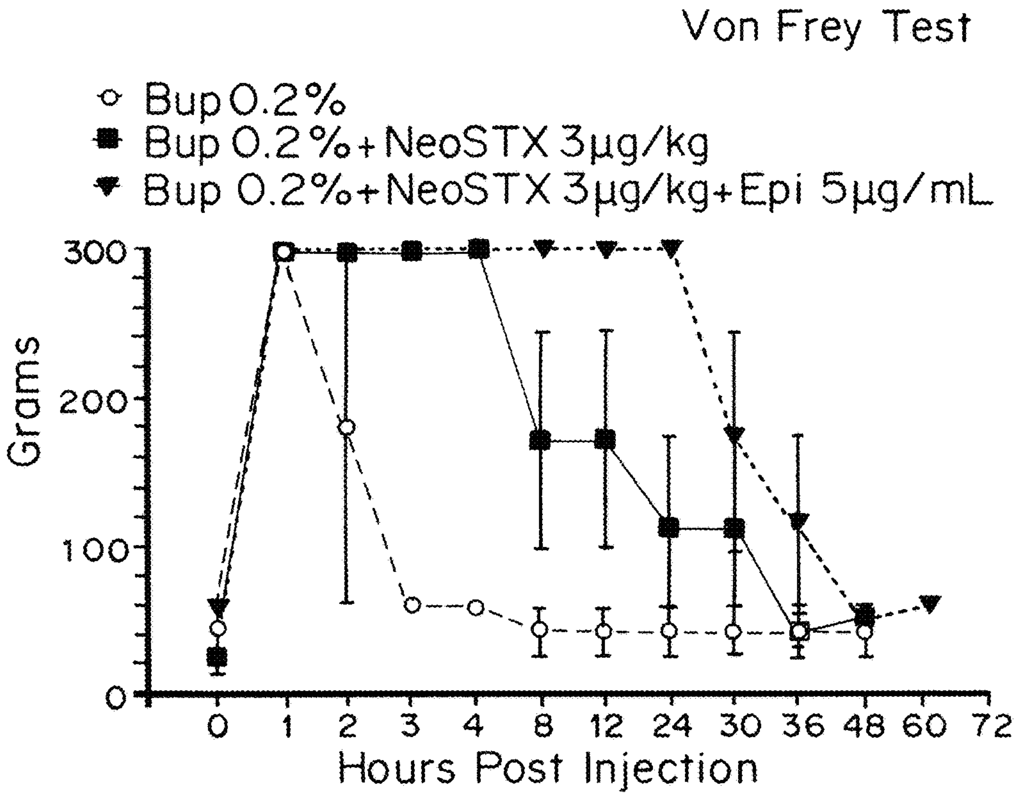

FIGS. 5A and 5B show the degree of sensory block. The Y-axis shows mechanical detection thresholds using von Frey filaments. Von Frey numbers are logarithmically related to grams of force applied. Numbers >16 represent fairly dense sensory block. Numbers 10-14 represent partial block and probably still contribute to degrees of postoperative analgesia. X-axis is time after injection. Error bars show SD.

Figure 6A:
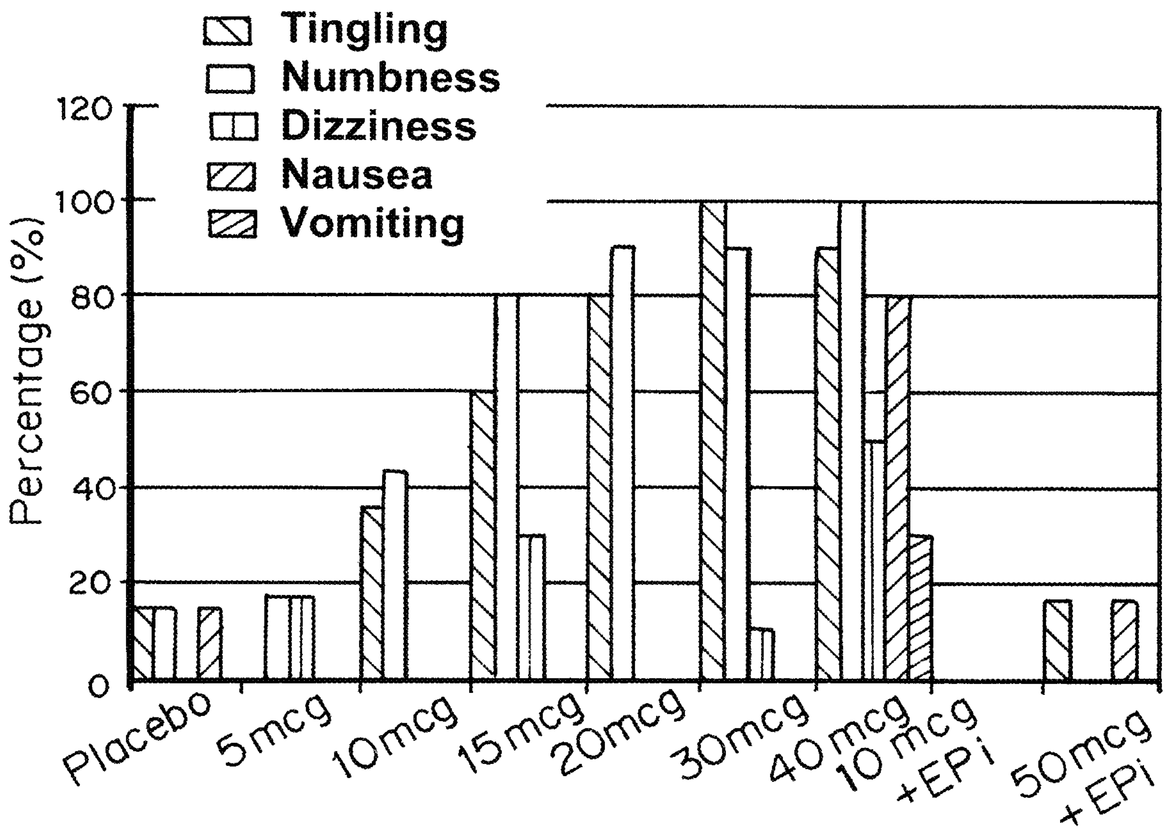
FIGS. 6A and 6B shown that the systemic symptoms in the Phase I human study varied with NeoSTX dose, with symptoms being greatly suppressed by inclusion of epinephrine. Addition of Epinephrine to NeoSTX-Bupivacaine combinations dramatically reduces the incidence and clinical significance of systemic symptoms at NeoSTX doses of 10 mcg and 30 mcg in adult humans in the Phase 1 Trial.
Figure 6B:
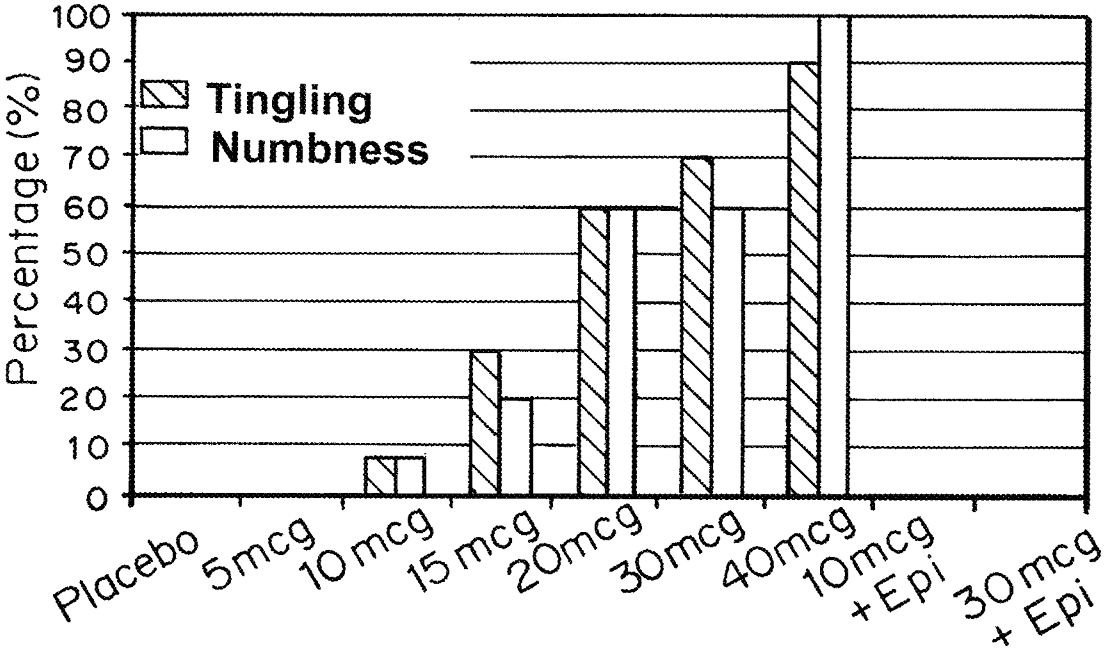

FIG. 6 is a graph of the percentage of subjects having systemic symptoms: tingling, numbness, dizziness, nausea or vomiting at any time point following administration of 0, 5, 10, 15, 20, 30 or 40 mcg NeoSTX-bupivacaine-epinephrine. Nausea was observed in 80% of subjects at 40 mcg NeoSTX.

No subject required medical intervention or supplemental oxygen. 02 sat, BP, NIF, VC, grip strength, ECG all very reassuring. For NeoSTX-Saline and NeoSTX-bupivacaine, transient mild tingling of lips, tongue and fingertips began at 10 mcg, with increasing tingling with escalation to 40 mcg Transient nausea and emesis at 40 mcg. Symptoms generally resolved within 1 hour. There were no local or systemic sequelae noted.

Figure 7A:
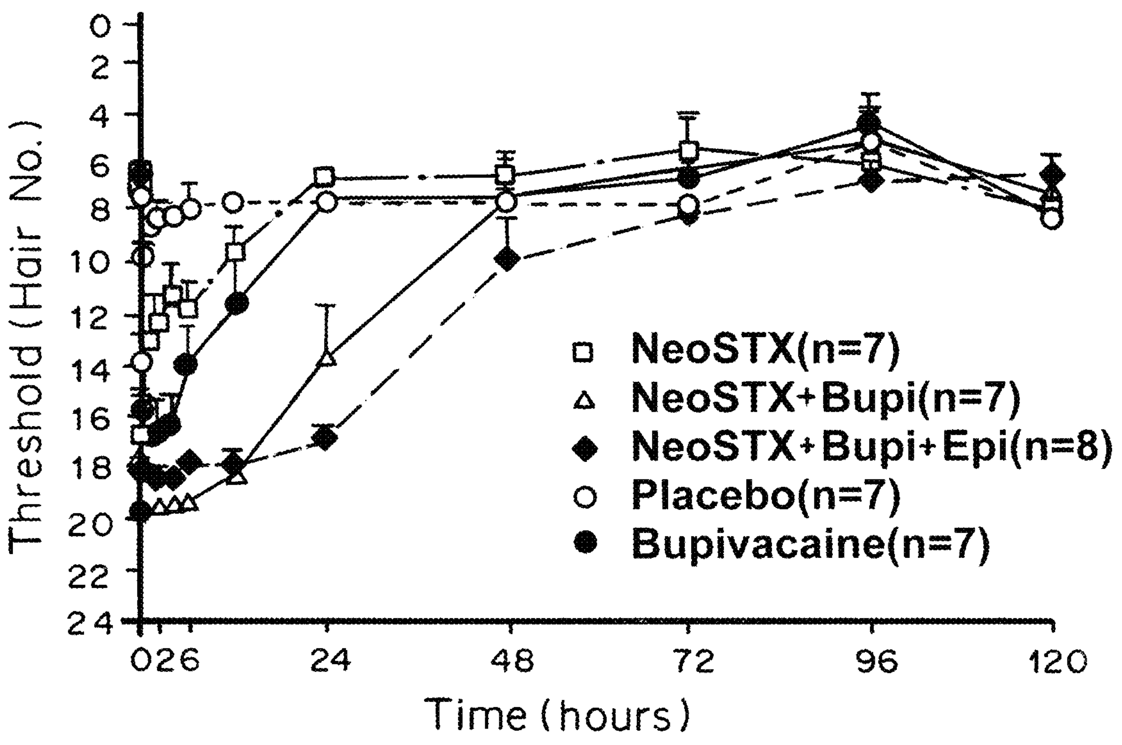
FIGS. 7A and 7B show the effects of NeoSTX-Bupivacaine and NeoSTX-Bupivacaine-Epinephrine combinations on block intensity and duration in Phase 1 human study using NeoSTX 10 mcg.
Figure 7B:
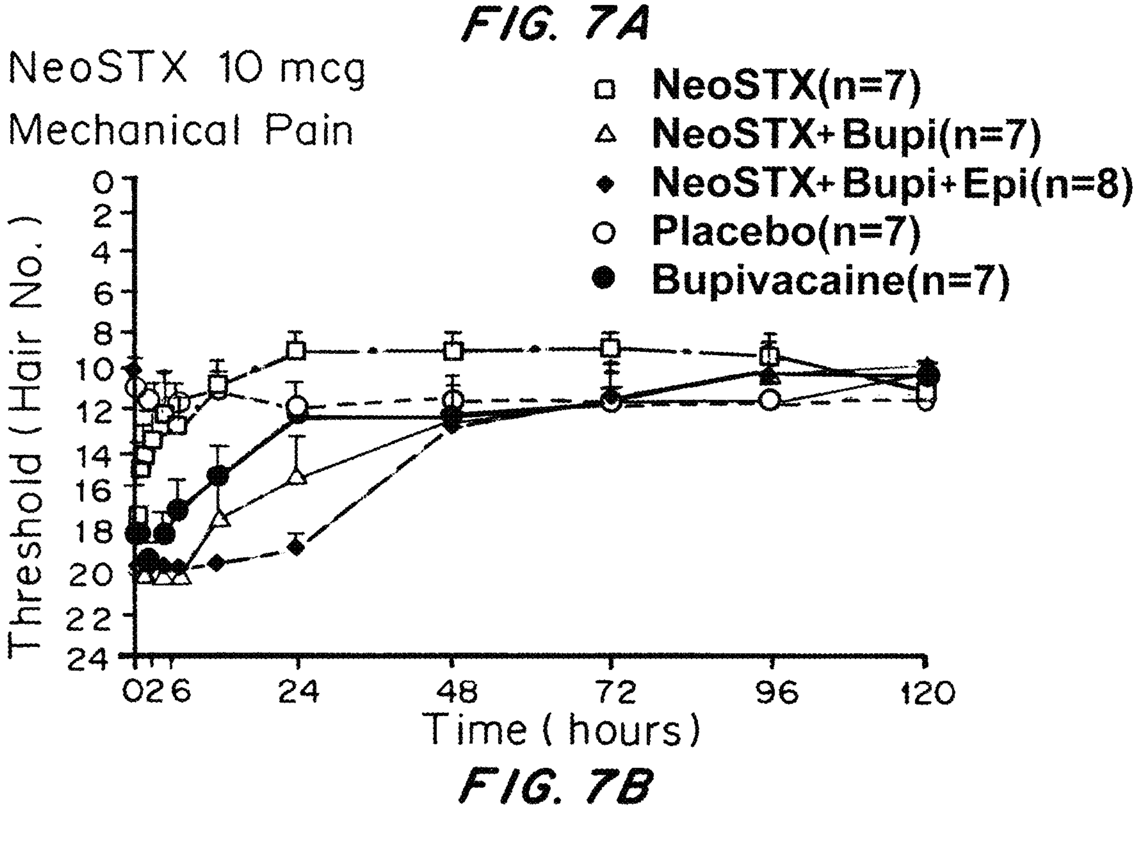
Figure 7C:
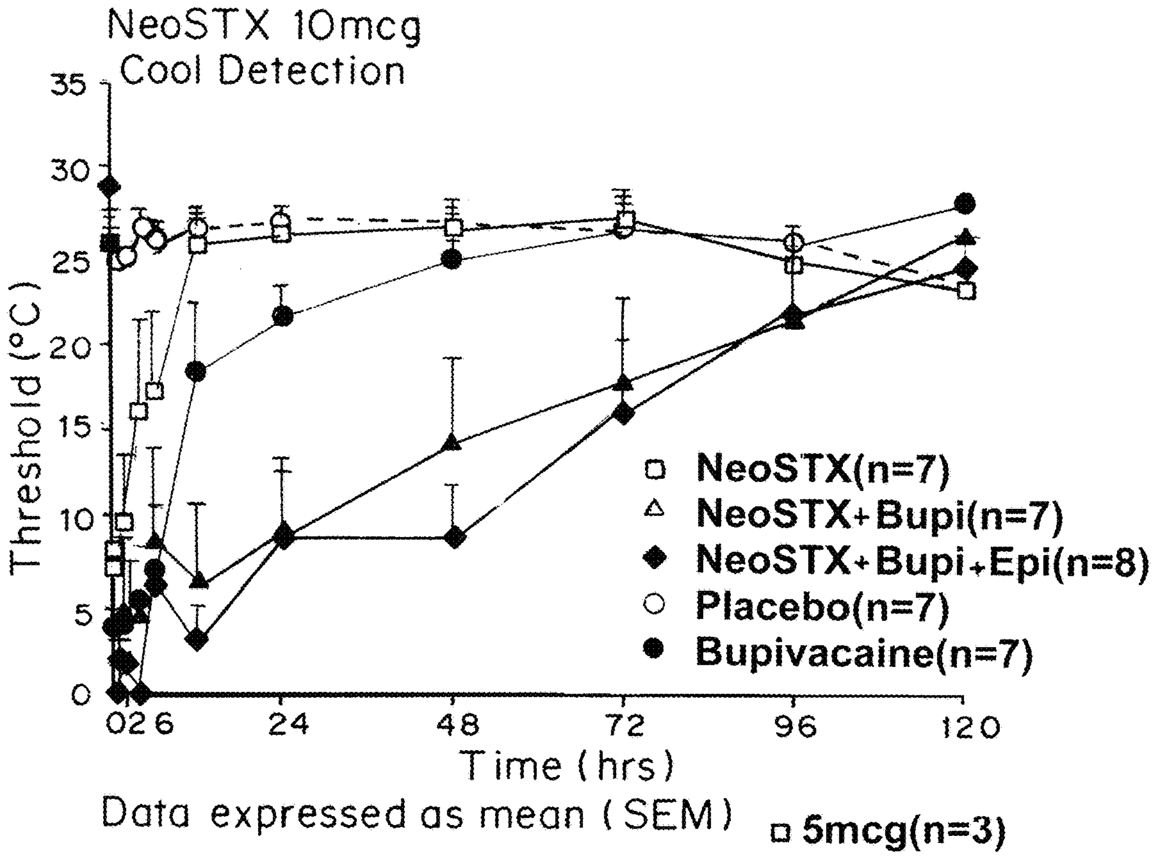
Figure 8A:
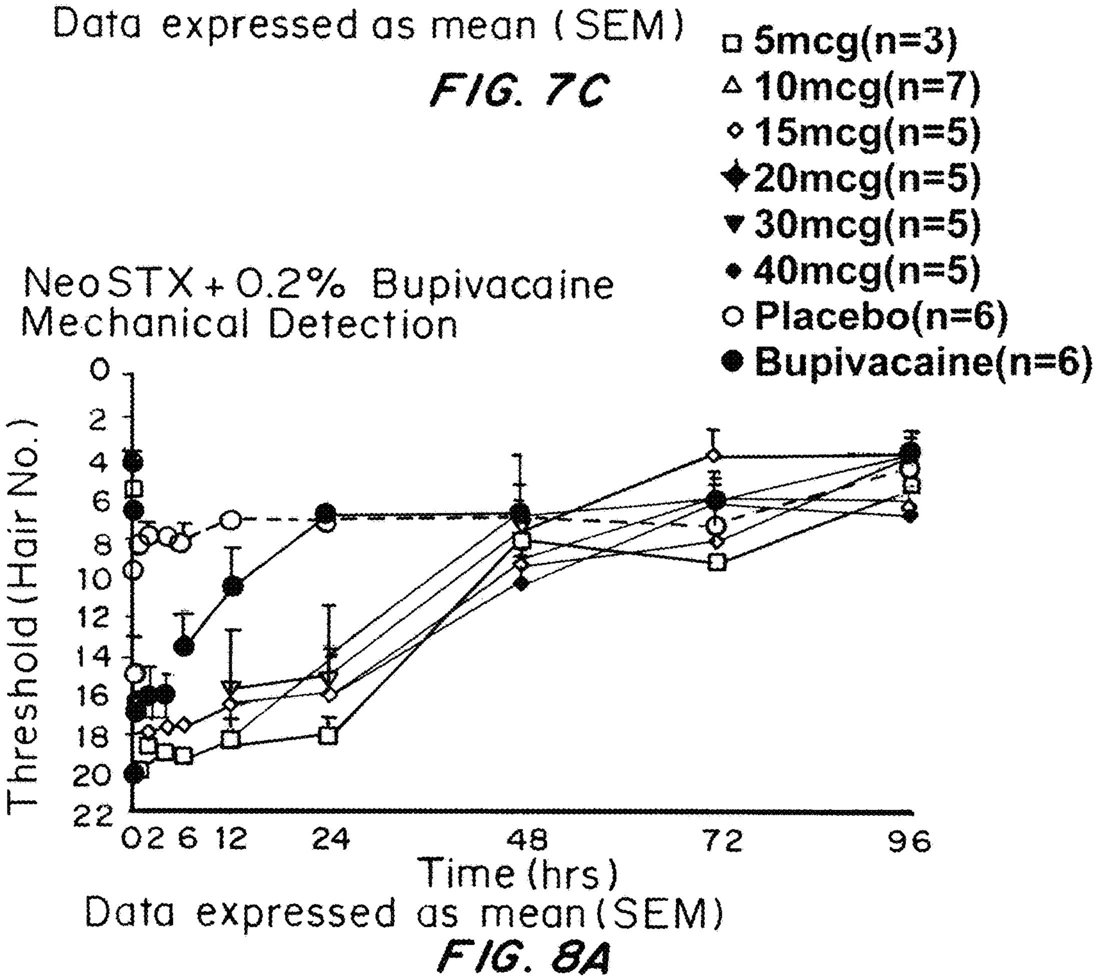
FIGS. 8A-8C show the effects of increasing NeoSTX Dose in NeoSTX-Bupivacaine 0.2% Combinations.
Figure 8B:
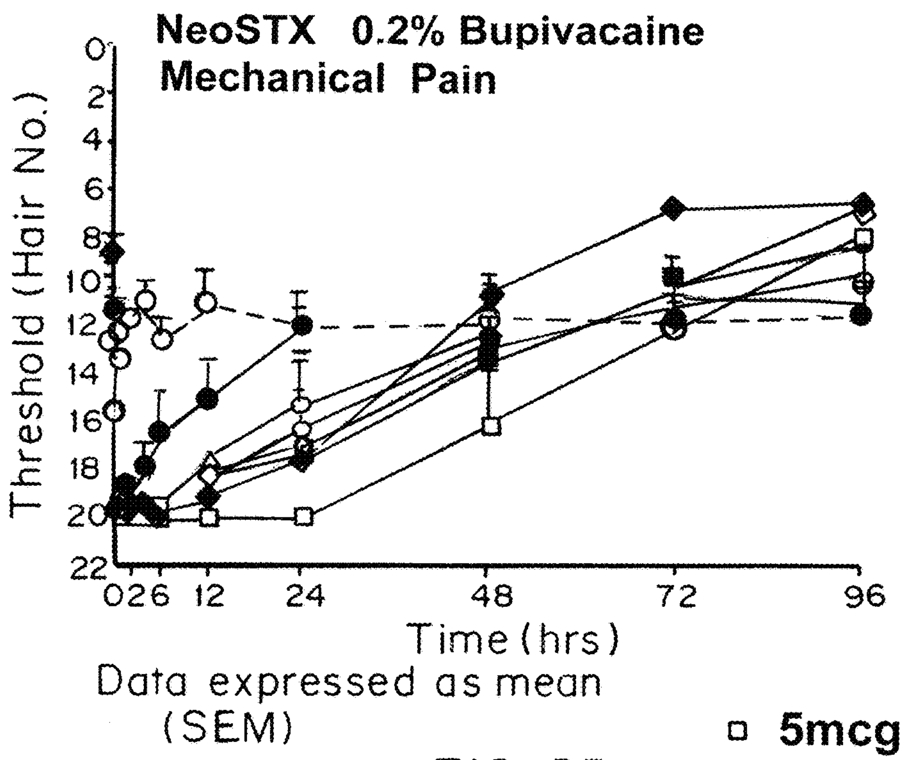
Figure 8C:
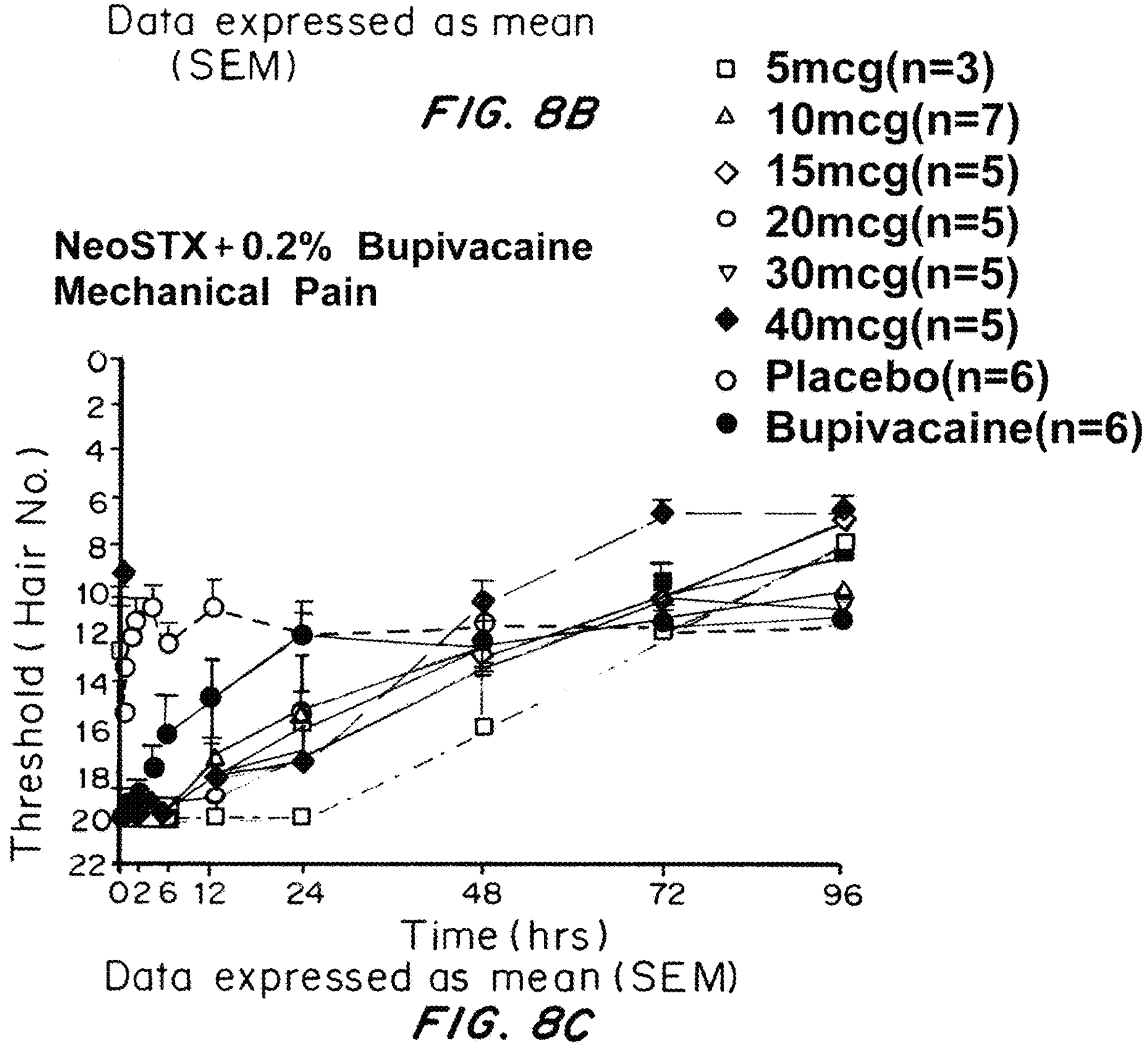

FIGS. 7A and 7B are graphs of the threshold measurement of dense and partial blockade, mechanical (FIG. 7A) and cool detection (FIG. 7B) for NeoSTX, NeoSTX+bupivacaine, NeoSTX+bupivacaine+epinephrine, compared to placebo and controls (no NeoSTX), over time in hours.

NeoSTX-Bupivacaine produces longer mechanical and thermal block than NeoSTX-plain or bupivacaine plain. NeoSTX-Bupivacaine gives reliable surgical anesthesia for 12 hours, reliable strong analgesia for >24 hours. Based on recovery of partial mechanical block, we predict that if these formulations are used for peripheral nerve blocks, motor block will not persist >24 hours, which is desirable. Based on recovery of partial mechanical block before recovery from partial thermal detection block (which correlates with pain sensation), a prolonged period of analgesia in the range from 24-48 hours, or even longer, with recovery of partial touch and motor function by 24 hours, is predicted.

NeoSTX-Bupivacaine-Epinphrine produces longer mechanical and thermal block than NeoSTX-bupivacaine, Neo-STX plain or bupivacaine plain. NeoSTX-Bupivacaine gives reliable surgical anesthesia/very dense analgesia for at least 24 hours. Based on duration of partial thermal detection block (which correlates with pain sensation), a prolonged period of postop analgesia in the range from 48-72 hours, or even longer, is predicted.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of making a dosage unit or kit for treatment or prevention of pain in a human, comprising providing neosaxitoxin, local anesthetic, epinephrine, and a diluent to produce the dosage unit or kit consisting of (a) neosaxitoxin in a concentration between 0.1 and 1 mcg neosaxitoxin/ml, (b) a local anesthetic selected from the group consisting of bupivacaine, levobupivacaine, tetracaine, and ropivacaine in a concentration between 0.1% (1 mg/ml) and 0.5% (5 mg/ml), (c) epinephrine in a concentration between 0 and 10 mcg/ml, and (d) a diluent.

2. The method of claim 1 wherein the dosage unit contains epinephrine in a concentration between 2 mcg/ml and 10 mcg/ml.

3. The method of claim 1 wherein the dosage unit contains (a) between 5 and 40 mcg of neosaxitoxin in a volume between about 5 ml and about 120 ml, inclusive, (b) a local anesthetic selected from the group consisting of bupivacaine, levobupivacaine and ropivacaine in a concentration of between 0.125% and 0.3% (between 1.25 and 3 mg/ml); and (c) epinephrine in a concentration between 0 and 10 mcg/ml.

4. The method of claim 1 wherein the dosage unit has a volume between 15 and 50 ml containing Bupivacaine, levobupivacaine or ropivacaine in a concentration of between 0.125% and 0.3% (between 1.25 and 3 mg/ml), giving a systemic dose in adults of no more than 150 mg or no more than 2 mg/kg in children, Neosaxitoxin in a concentration between 0.2 and 1 mcg/ml, giving a systemic dose in adult humans of between 7 and 100 mcg, and Epinephrine in a concentration between 0 and 10 mcg/ml.

5. The method of claim 1 wherein the dosage unit has a volume between 15 and 50 ml containing Bupivacaine, levobupivacaine or ropivacaine in a concentration between 1.25 and 3 mg/ml, giving a systemic dose of no more than 2 mg/kg in children, and Neosaxitoxin in a concentration between 0.2 and 1 mcg/ml, and Epinephrine in a concentration between 0 and 10 mcg/ml.

6. The method of claim 1 wherein the dosage unit contains

Bupivacaine, levobupivacaine or ropivacaine in a concentration of between 2.5 and 5 mg/ml, wherein between 5 and 15 ml gives a systemic bupivacaine dose in adults of no more than 75 mg.

7. The method of claim 1 wherein the dosage unit contains epinephrine in a concentration between 2.5 mcg/ml and 7.5 mcg/ml.

8. The method of claim 1 wherein the neosaxitoxin is added to a total amount of 5 μg of neosaxitoxin.

9. The method of claim 1, wherein the local anesthetic is bupivacaine in a concentration of between 2 and 5 mg/mL.

10. The method of claim 1, wherein the epinephrine is in a total amount of 0.1 mg epinephrine.

11. The method of claim 1, wherein the epinephrine is added to neosaxitoxin and bupivacaine to a total amount of 0.1 mg epinephrine.

12. The method of claim 1, wherein epinephrine is added to the neosaxitoxin and local anesthetic to a total amount of 0.2 mg epinephrine.

13. A method of making a kit to provide a dosage unit for treatment or prevention of pain in a human, comprising providing a kit comprising neosaxitoxin, local anesthetic, epinephrine and a diluent to produce a dosage unit consisting of (a) neosaxitoxin in a concentration between 0.1 and 1 mcg neosaxitoxin/ml, (b) a local anesthetic selected from the group consisting of bupivacaine, levobupivacaine, tetracaine, and ropivacaine in a concentration between 0.1% (1 mg/ml) and 0.5% (5 mg/ml), and (c) epinephrine in a concentration between 0 and 10 mcg/ml, and (d) a diluent, wherein any one or more of the neosaxitoxin, local anesthetic and epinephrine is in powder or lyophilized form and is in combination with an appropriate amount of the diluent.

14. The method of claim 1, wherein any one or more of the neosaxitoxin, local anesthetic and epinephrine is in the form of a solution.

* * * * *